United States Patent
Cree et al.

[11] Patent Number: 6,103,953
[45] Date of Patent: *Aug. 15, 2000

[54] ABSORBENT ARTICLE HAVING FUSED LAYERS

[75] Inventors: James William Cree, Mundelein, Ill.; Sue Ann Mills, Cincinnati, Ohio; Elizabeth Bilyeu Twohy, Hunt Valley, Md.; Kenneth Barclay Buell, Cincinnati, Ohio

[73] Assignee: The Procter & Gamble Company, Cincinnati, Ohio

[*] Notice: This patent is subject to a terminal disclaimer.

[21] Appl. No.: 09/127,212

[22] Filed: Jul. 31, 1998

Related U.S. Application Data

[63] Continuation of application No. 08/811,330, Mar. 4, 1997, abandoned, which is a continuation of application No. 07/944,764, Sep. 14, 1992, abandoned, which is a continuation-in-part of application No. 07/810,774, Dec. 17, 1991, abandoned.

[51] Int. Cl.[7] .................................................. A61F 13/20
[52] U.S. Cl. .......................... 604/365; 604/366; 604/370; 604/378
[58] Field of Search ........................... 604/358, 365–368, 604/370, 378–381, 384–385.2; 428/137, 138, 296.7

[56] References Cited

U.S. PATENT DOCUMENTS

| | | |
|---|---|---|
| D. 253,425 | 11/1979 | Roeder . |
| D. 253,550 | 11/1979 | Roeder . |
| 3,285,245 | 11/1966 | Eldredge et al. . |
| 3,292,619 | 12/1966 | Egler . |
| 3,545,441 | 12/1970 | Gravdahl . |
| 3,727,615 | 4/1973 | Duchane .................................. 604/384 |
| 3,929,135 | 12/1975 | Thompson . |
| 3,945,386 | 3/1976 | Anczwoski et al. . |
| 3,965,906 | 6/1976 | Karami . |
| 3,967,623 | 7/1976 | Butterworth et al. . |
| 3,976,074 | 8/1976 | Fitzgerald et al. . |
| 3,994,299 | 11/1976 | Karami . |
| 4,014,341 | 3/1977 | Karami . |
| 4,047,531 | 9/1977 | Karami . |
| 4,054,141 | 10/1977 | Schwaiger et al. . |
| 4,077,410 | 3/1978 | Butterworth et al. .................... 604/378 |
| 4,082,886 | 4/1978 | Butterworth et al. . |
| 4,129,132 | 12/1978 | Butterworth et al. . |
| 4,184,902 | 1/1980 | Karami . |
| 4,214,582 | 7/1980 | Patel . |
| 4,219,024 | 8/1980 | Patience et al. . |
| 4,285,343 | 8/1981 | McNair . |
| 4,315,507 | 2/1982 | Whitehead et al. . |
| 4,324,247 | 4/1982 | Aziz . |
| 4,342,314 | 8/1982 | Radel et al. . |

(List continued on next page.)

FOREIGN PATENT DOCUMENTS

| | | |
|---|---|---|
| 52-230495 | 9/1987 | Japan . |
| WO 93/09744 | 5/1993 | WIPO . |

OTHER PUBLICATIONS

Dr. Hermann Diehl, submission on behalf of opponent Kimberly–Clark in opposition against European equivalent of the present patent application, dated Feb. 9, 2000 (discussed in greater detail in Supplemental Information Disclosure Statement).

*Primary Examiner*—Mark O. Polutta
*Attorney, Agent, or Firm*—Jeffrey V. Bamber

[57] ABSTRACT

An absorbent article, such as a diaper, sanitary napkin, adult incontinent device, and the like having fused layers is provided. The absorbent articles preferably comprises a liquid pervious thermoplastic apertured film topsheet, a liquid impervious backsheet, an absorbent core, and a fibrous acquisition web. The absorbent core is positioned between the topsheet and backsheet which are joined at least about a portion of the periphery of the absorbent article and the topsheet is fused to the acquisition web is a folded sheet which has a double z-folded cross-sectional configuration, which at discrete points of attachment. The acquisition web is positioned between the topsheet and the absorbent core.

2 Claims, 16 Drawing Sheets

U.S. PATENT DOCUMENTS

| | | |
|---|---|---|
| 4,392,861 | 7/1983 | Matthews et al. . |
| 4,397,644 | 8/1983 | Matthews et al. ............. 604/378 |
| 4,443,512 | 4/1984 | Delvaux . |
| 4,475,911 | 10/1984 | Gellert . |
| 4,518,451 | 5/1985 | Luceri et al. ............. 604/378 |
| 4,589,876 | 5/1986 | Van Tilburg . |
| 4,623,340 | 11/1986 | Luceri . |
| 4,636,209 | 1/1987 | Lassen . |
| 4,659,614 | 4/1987 | Vitale . |
| 4,676,786 | 6/1987 | Nishino ............. 604/378 |
| 4,687,478 | 8/1987 | Van Tilburg . |
| 4,690,679 | 9/1987 | Mattingly et al. . |
| 4,726,976 | 2/1988 | Karami et al. . |
| 4,752,349 | 6/1988 | Gebel . |
| 4,753,840 | 6/1988 | Van Gompel . |
| 4,780,352 | 10/1988 | Palumbo . |
| 4,781,962 | 11/1988 | Zamarripa et al. . |
| 4,798,603 | 1/1989 | Meyer et al. . |
| 4,823,783 | 4/1989 | Willhite, Jr. et.al. . |
| 4,844,965 | 7/1989 | Foxman . |
| 4,854,984 | 8/1989 | Ball et al. . |
| 4,908,026 | 3/1990 | Sukiennik et al. . |
| 4,917,697 | 4/1990 | Osborn et al. . |
| 4,950,264 | 8/1990 | Osborn . |
| 4,994,037 | 2/1991 | Bernardin ............. 604/378 |
| 5,007,906 | 4/1991 | Osborn et al. . |
| 5,009,653 | 4/1991 | Osborn . |
| 5,135,521 | 8/1992 | Luceri et al. . |
| 5,269,994 | 12/1993 | Deffenbaugh et al. . |
| 5,281,208 | 1/1994 | Thompson et al. . |
| 5,300,054 | 4/1994 | Feist et al. . |
| 5,324,278 | 6/1994 | Visscher et al. . |
| 5,460,622 | 10/1995 | Dragoo et al. ............. 604/378 |
| 5,591,149 | 1/1997 | Cree et al. ............. 604/378 |
| 5,762,641 | 6/1998 | Bewick-Sonntag et al. ............. 604/378 |

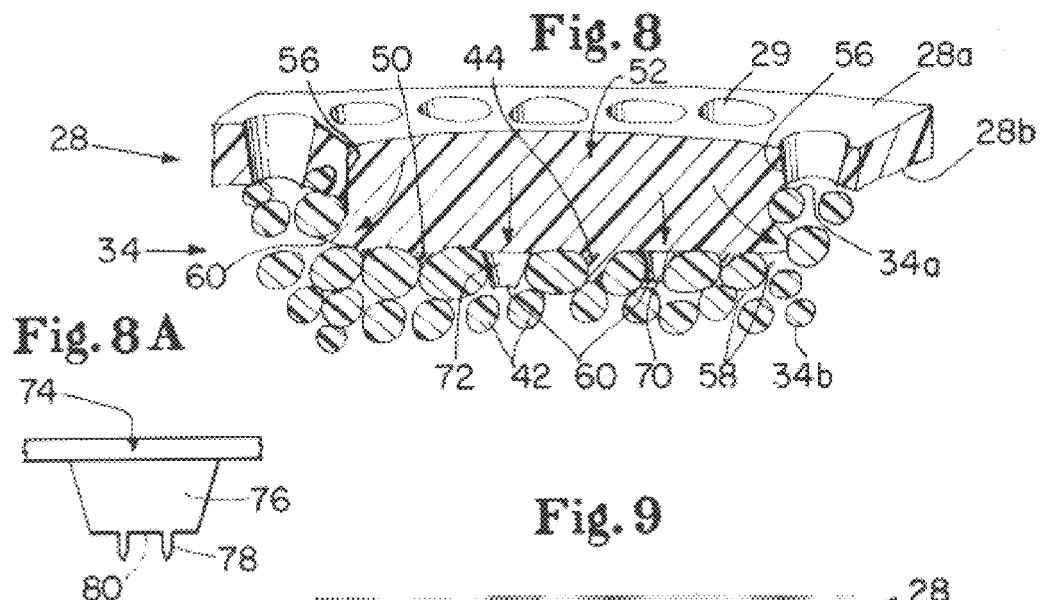
Fig. 8
Fig. 8A
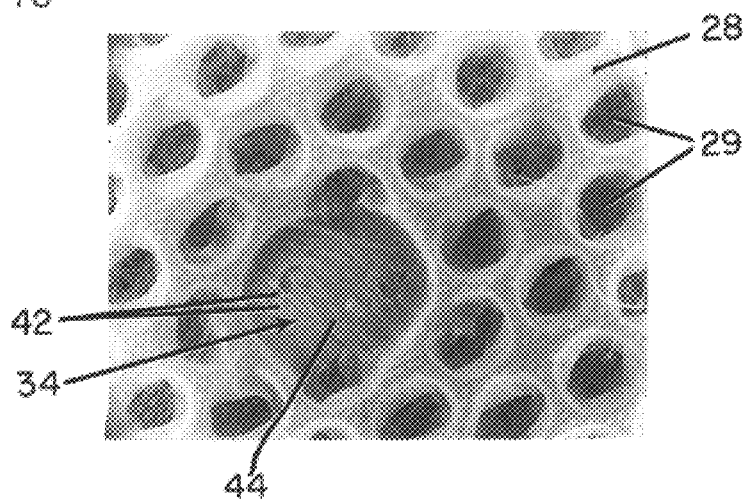
Fig. 9
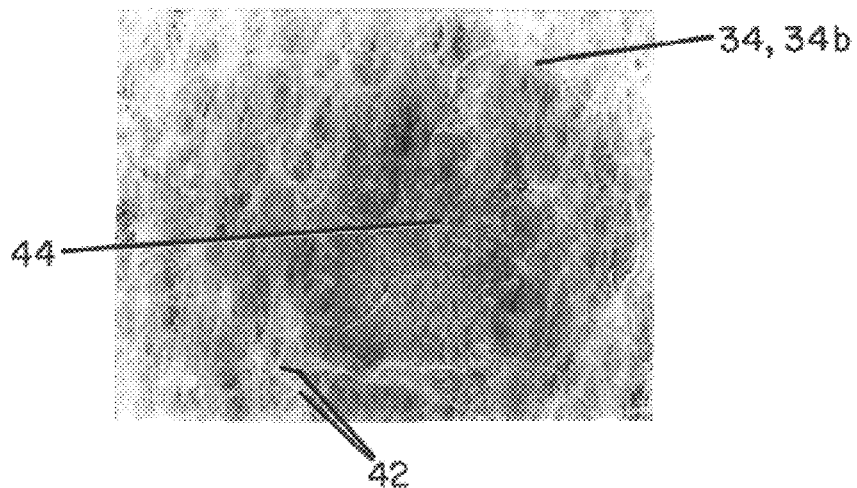
Fig. 10

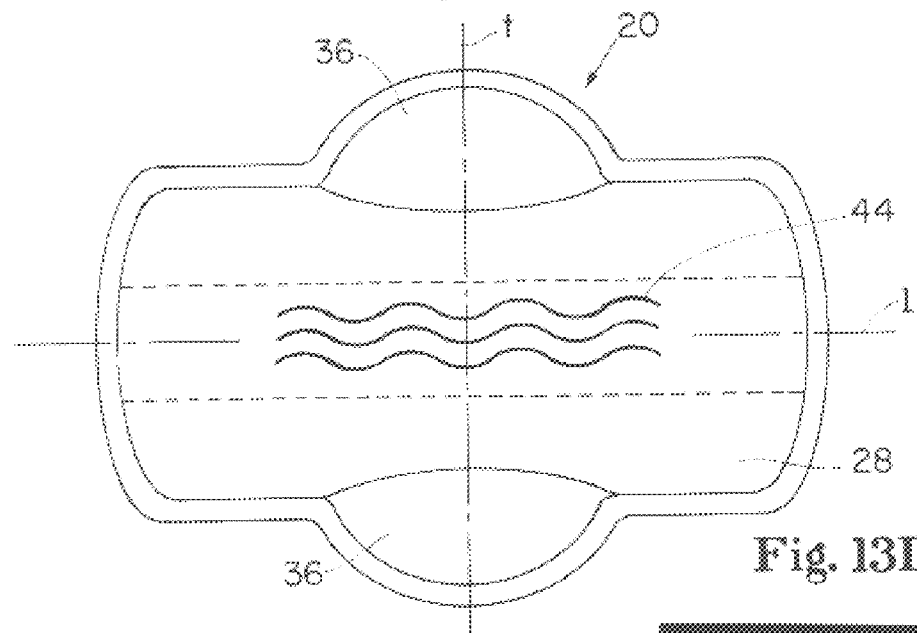
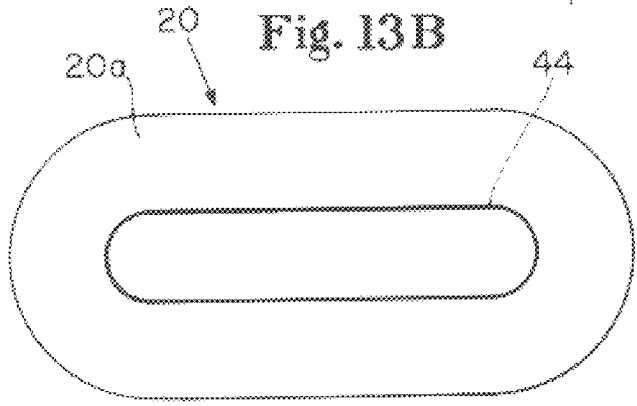
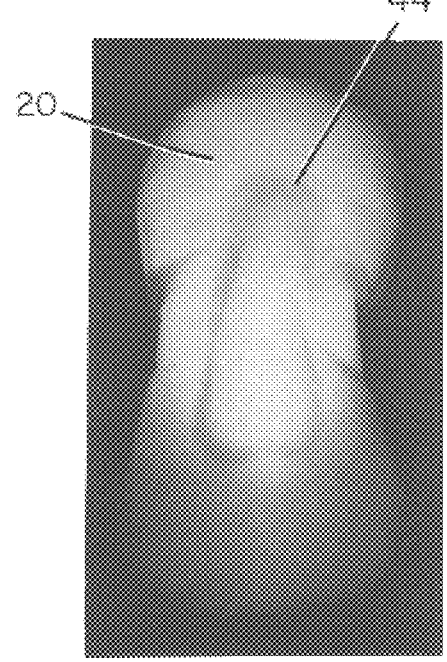
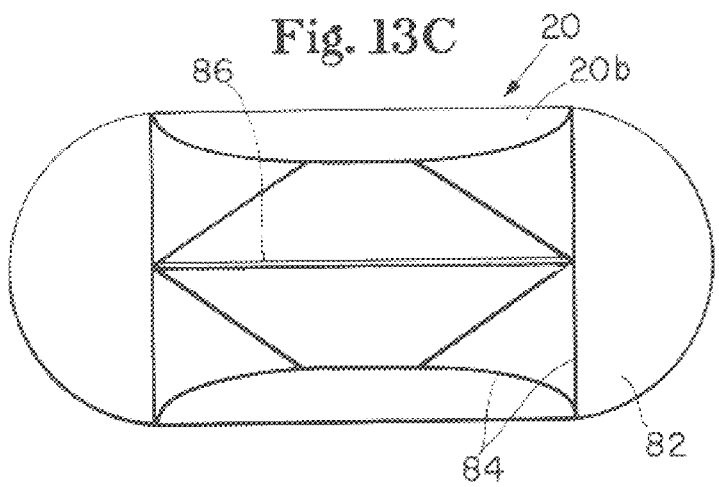
Fig. 13A
Fig. 13B
Fig. 13C
Fig. 13D $$R = \frac{2\gamma \cos\theta_{rec(adv)}}{\Delta P}$$

ABSORBENT ARTICLE HAVING FUSED LAYERS

This is a continuation of application Ser. No. 08/811,330, filed on Mar. 4, 1997, abandoned, which is a continuation of application Ser. No. 07/944,764, filed on Sep. 14, 1992, abandoned, which was a continuation-in-part of application Ser. No. 07/810,774 filed on Dec. 17, 1991, now abandoned.

FIELD OF THE INVENTION

The present invention relates to absorbent articles such as diapers, sanitary napkins, adult incontinence devices, and the like which have fused layers.

BACKGROUND OF THE INVENTION

All manner and variety of absorbent articles configured for the absorption of body fluids such as menses, urine, and feces are, of course, well known. Absorbent articles are typically comprised of a number of layers of material. These generally include, from top to bottom, a liquid pervious layer, an absorbent layer, and a liquid impervious layer. Additional layers may also be interposed between any of these layers. Such additional layers may serve various different purposes.

These layers are generally held together around their peripheries by some conventional means, such as adhesives, crimping, fusing, and other methods known in the art. The absorbent articles can have, and in many cases preferably will have, a liquid impermeable bond around their periphery. This will not interfere with the function of the absorbent article. However, it is frequently also desirable to bond the layers together at their faces. The attachment of the faces of these layers presents certain technical problems. This is particularly the case when it is desired to attach the upper liquid pervious layers and absorbent layers. The same means used for attaching the layers at their peripheries cannot be used because they will tend to block the flow of liquids to the absorbent layer.

A number of attempts have been made to deal with this problem. These have included utilizing hot melt adhesives, and other non-water based adhesives. Such adhesives will be less likely to dissolve when contacted by body liquids. Other attempts have been directed at applying adhesives in very thin layers or in particular patterns to attempt to minimize the interference with the flow of liquids to the underlying layers. U.S. Pat. No. 4,573,986 issued to Minetola, et al. on Mar. 4, 1986 discloses one preferred way of applying adhesives. Although the application of adhesives in the manner described in the Minetola, et al. patent works quite well, the search for improved ways of securing the faces of the layers of absorbent products has continued.

The main reason for searching for improved ways of securing the faces of such layers is that in many cases, adhesives which initially function adequately, may eventually fail and cause the liquid pervious layer to become unattached. This problem is particularly apparent during prolonged use of an absorbent article. This problem is often heightened when the liquid pervious layer is an apertured plastic film. While apertured plastic films made according to the patents owned by the assignee of the present invention perform very well, certain problems can occur when they separate from their underlying layers. The plastic films are sufficiently thin that they can move well into the crevices of the wearer's body (such as the space between the wearer's buttocks) when they become unattached. This can be extremely uncomfortable and irritating. Because of its plastic composition, in some of these instances, the liquid pervious layer may even stick to the skin of the wearer. The adhesives may cause the film to present a sticky surface near the body of the wearer which aids in causing the liquid pervious layer to stick to the skin of the wearer.

The separation of the formed film from the absorbent layers also often causes exudates to run off the top of the product along the longitudinal edges. The exudates will not penetrate the film since there is no longer an underlying absorbent layer in contact with the film for the exudates to wick into. This is particularly true in the case of thick pads having airfelt batts for their absorbent cores. The absorbent core of such thick pads tends to collapse and bunch or gather in transversely in the center of the product upon the first incidence of wetting. This gathering in, combined with the separation of the formed film, leaves the portion of the pad adjacent its longitudinal edges without any underlying absorbent material, thereby increasing the possibility of runoff or leakage on top of the product along the longitudinal edges.

Several patents describe absorbent products having layers held together in alternative manners for various different purposes. Such efforts are described in U.S. Pat. Nos. 3,965,906 and 4,184,902 issued to Karami, U.S. Pat. No. 4,391,861 issued to Butterworth, et al., U.S. Pat. No. 4,397,644 issued to Matthews, et al., U.S. Pat. No. 4,475,911 issued to Gellert, U.S. Pat. No. 4,726,976 issued to Karami, et al., U.S. Pat. No. 4,752,349 issued to Gebel, U.S. Pat. No. 4,753,840 issued to Van Gompel, U.S. Pat. No. 4,823,783 issued to Willhite, Jr., et al., U.S. Pat. No. 4,844,965 issued to Foxman, and U.S. Pat. No. 4,908,026 issued to Sukiennick, et al. The majority of these patents, however, do not disclose fusing an apertured formed film on top of a nonwoven material. It is believed that those and any others are not directed to the use of fusion to create bond sites that do not interfere with the acquisition of liquids into the absorbent layer.

Thus, a need exists for absorbent articles having improved bonding between their layers, particularly between the uppermost fluid pervious layers.

Therefore, it is an object of the present invention to provide absorbent articles having bonding between their layers, particularly the uppermost liquid pervious layers, that maintain sustained attachment even under prolonged use.

It is another object of the present invention to provide absorbent articles having liquid pervious layers bonded at bond sites that provide structures that do not interfere with the acquisition of liquids into the absorbent layer.

It is still another object of the present invention to provide an absorbent article that can be visually observed by the wearer as having the potential for aiding in the absorption of liquids.

These and other objects of the present invention will be more readily apparent when considered in reference to the following description and when taken in conjunction with the accompanying drawings.

SUMMARY OF THE INVENTION

In accordance with the present invention, an absorbent article, such as a diaper, a sanitary napkin, or an adult incontinence device, or the like which has fused layers is provided.

The absorbent article preferably comprises a liquid pervious apertured thermoplastic film topsheet, a liquid impervious backsheet joined to the topsheet, an absorbent core, and an acquisition layer.

The absorbent core is positioned between the topsheet and the backsheet. The acquisition layer preferably comprises a fibrous web. The acquisition layer may either be a separate web positioned between the topsheet and the absorbent core, or it may comprise part of the topsheet or part of the core (or other element). In one embodiment, the acquisition layer is a folded sheet which has a double z-folded cross-sectional configuration. The topsheet and backsheet are joined together along at least a portion of the periphery of the absorbent article. The topsheet and the acquisition layer (or other underlying layer) are placed in a face-to-face relationship. The topsheet is secured to such an underlying layer (or layers) at discrete bonded areas. At least some of the bonded areas provide structures with drainage passageways for liquids to pass through to the absorbent core.

The fusion of the faces of the topsheet and the acquisition layer maintains these layers in an attached condition, even under prolonged use. The attachment is believed to accomplish the objects set forth above, among others. The attachment is also believed to create bond sites that provide structures which do not interfere with the acquisition of liquids into the absorbent core. The sustained attachment also facilitates absorption of liquids into the absorbent core by maintaining an underlying absorbent layer in constant contact with the apertured film topsheet.

BRIEF DESCRIPTION OF THE DRAWINGS

FIG. 8 is a simplified and greatly enlarged schematic cross-sectional view of a bond site where the topsheet of the sanitary napkin is fused to an underlying fibrous acquisition layer.

FIG. 8A is a schematic side view of part of a device that could be used to create a fusion bond.

FIGS. 9 and 10 are greatly enlarged top and bottom plan view photographs of the fused layers in the area of typical bond sites.

FIG. 13A is a plan view of a sanitary napkin provided with an alternative bond pattern.

FIGS. 13B–13D are top and bottom plan views and a perspective view photograph of a sanitary napkin provided with another alternative bond pattern.

DETAILED DESCRIPTION OF PREFERRED EMBODIMENTS

1. Introduction

Figure 1:
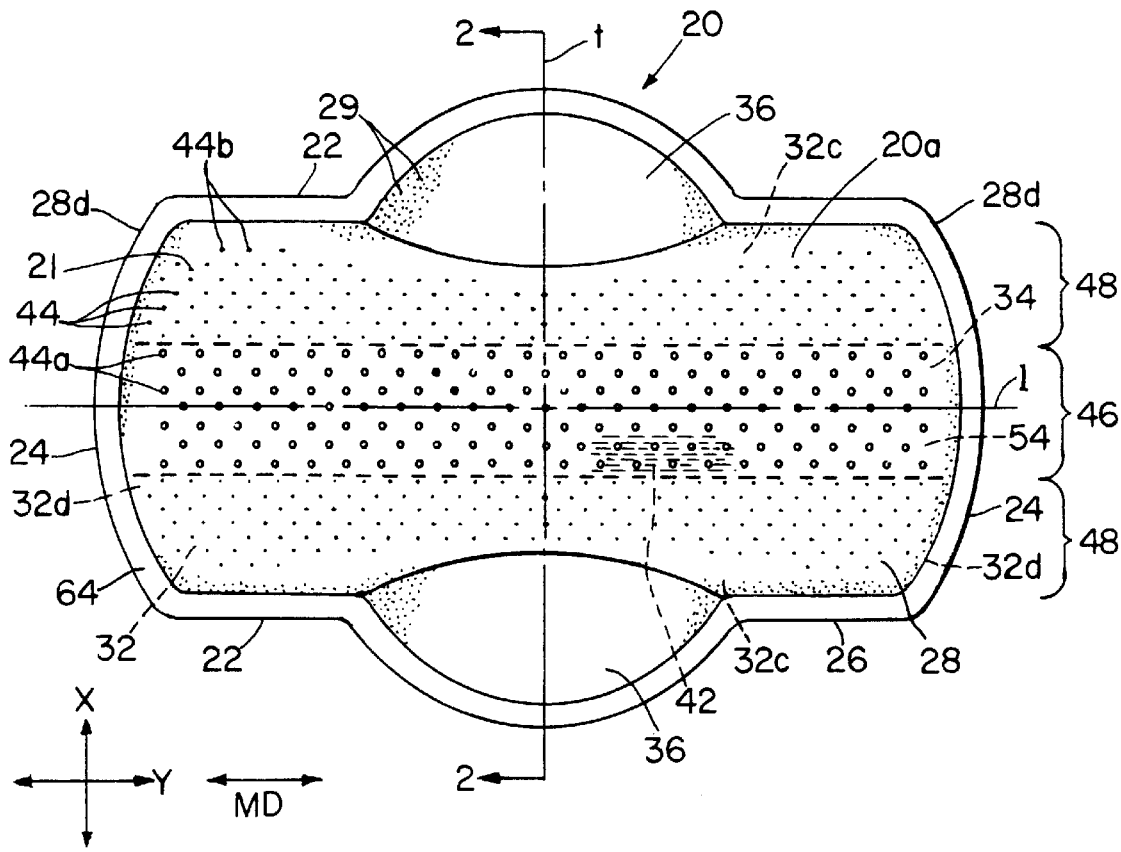
FIG. 1 is a top plan view of a preferred sanitary napkin embodiment of the present invention.

The present invention relates to absorbent articles such as diapers, sanitary napkins, adult incontinence devices, and the like, which have fused layers.

The term "absorbent article", as used herein, refers to articles which absorb and contain body exudates. More specifically, the term refers to articles which are placed against or in proximity to the body of the wearer to absorb and contain the various exudates discharged from the body. The term "absorbent article" is intended to include diapers, sanitary napkins, pantiliners, and incontinent pads, and the like. The term "disposable" refers to articles which are intended to be discarded after a single use and preferably recycled, composted, or otherwise disposed of in an environmentally compatible manner. (That is, they are not intended to be laundered or otherwise restored or reused as an absorbent article.) In the preferred embodiment illustrated, the absorbent article is a sanitary napkin designated 20.

The term "sanitary napkin", as used herein, refers to an article which is worn by females adjacent to the pudendal region that is intended to absorb and contain the various exudates which are discharged from the body (e.g., blood, menses, and urine). The present invention, however, is not limited to the particular types or configurations of absorbent articles shown in the drawings.

The sanitary napkin 20 has two surfaces, a body-contacting surface or "body surface" 20a and a garment surface 20b. The sanitary napkin 20 is shown in FIG. 1 as viewed from its body surface 20a. The body surface 20a is intended to be worn adjacent to the body of the wearer. The garment surface 20b of the sanitary napkin 20 (shown in FIG. 2) is on the opposite side and is intended to be placed adjacent to the wearer's undergarments when the sanitary napkin 20 is worn.

The sanitary napkin 20 has two centerlines, a longitudinal centerline 1 and a transverse centerline 1. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction. FIG. 1 shows that the sanitary napkin 20 also has two spaced apart longitudinal or side edges 22 and two spaced apart transverse or end edges (or "ends") 24, which together form the periphery 26 of the sanitary napkin 20.

The sanitary napkin 20 can be of any thickness, including relatively thick or relatively thin. The embodiment of the sanitary napkin 20 shown in FIGS. 1–3 of the drawings is intended to be an example of a relatively thin sanitary napkin. It should be understood, however, when viewing these figures the number of layers of material shown cause the sanitary napkin 20 to appear much thicker than it actually is. A "thin" sanitary napkin 20 preferably has a caliper of less than about 3 millimeters. The thin sanitary napkin 20 shown should also be preferably relatively flexible, so that it is comfortable for the wearer.

Figure 2:
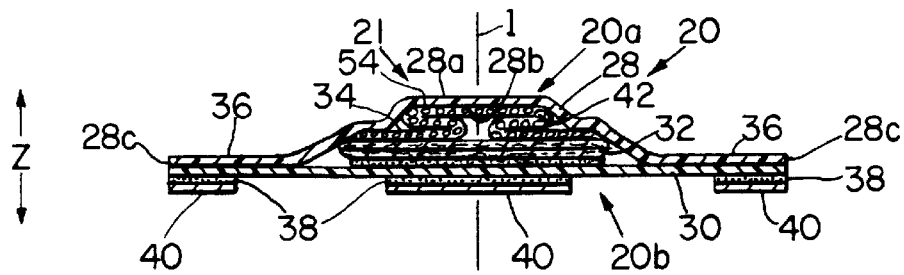
FIG. 2 is a simplified transverse cross-sectional view taken along line 2—2 of FIG. 1.

FIG. 2 shows the individual components of the sanitary napkin. The sanitary napkin 20 of the present invention generally comprises at least three primary components. These include a liquid pervious topsheet 28, a liquid impervious backsheet (or "barrier means") 30, and an absorbent core 32. The absorbent core 32 is positioned between the topsheet 28 and the backsheet 30. The sanitary napkin 20 also comprises a liquid pervious acquisition layer (or acquisition sheet) 34. The acquisition layer 34 may be a separate element positioned between the topsheet 28 and the absorbent core 32, or it may comprise part of the topsheet 28 or part of the core 32. The sanitary napkin 20 preferably also includes optional side flaps or "wings" 36 that are folded around the crotch portion of the wearer's panties. The sanitary napkin 20 shown also has an adhesive fastening means 38 for attaching the sanitary napkin 20 to the undergarment of the wearer. Removable release liners 40 cover the adhesive fastening means 38 to keep the adhesive from sticking to a surface other than the crotch portion of the undergarment prior to use.

2. Individual Components of the Absorbent Article

The individual components of the sanitary napkin 20 will now be looked at in greater detail.

A. The Topsheet

The topsheet 28 comprises a first liquid pervious component. When the sanitary napkin 20 is in use, the topsheet 28 is in close proximity to the skin of the user. The topsheet 28 is preferably as compliant, soft feeling, and non-irritating to the user's skin as possible. The topsheet 28 should further exhibit good strikethrough and a reduced tendency to rewet, permitting bodily discharges to rapidly penetrate it and flow toward the core 32, but not allowing such discharges to flow back through the topsheet 28 to the skin of the wearer.

The topsheet 28 has two sides (or faces or surfaces), including a body-facing side 28a and a garment-facing side (or core-facing side) 28b. The body-facing side 28a of the topsheet 28 generally forms at least a portion of the body-contacting surface ("body surface") 20a of the sanitary napkin 20. The topsheet 28 has two longitudinal edges 28c and two end edges 28d. (A similar numbering system will be used for the other components of the sanitary napkin. That is, the side of the component facing the wearer's body will be designated by the number of the component and a reference letter "a". The side facing the wearer's undergarments will be designated by the number of the component and the letter "b". The side and end edges will be designated by the number of the component and the reference letters "c" and "d" respectively.)

A suitable topsheet 28 may be manufactured from a wide range of materials including, but not limited to woven and nonwoven materials, apertured formed thermoplastic films, apertured plastic films, hydro-formed films, porous foams, reticulated foams, reticulated thermoplastic films, and thermoplastic scrims. Suitable woven and nonwoven materials can be comprised of natural fibers (e.g., wood or cotton fibers), synthetic fibers (e.g., polymeric fibers, such as polyester, polypropylene fibers, and polyethylene, or polyvinylalcohol, starch base resins, polyurethanes, cellulose esters, nylon, and rayon fibers) or from a combination of natural and synthetic fibers. Apertured formed films are generally preferred for the topsheet 28 because they are pervious to liquids and, if properly apertured, have a reduced tendency to allow liquids to pass back through and rewet the wearer's skin.

FIG. 1 shows that the formed film topsheet 28 is provided with a multiplicity of apertures 29. The apertures 29 are shown only in portions of the topsheet 28 overlying the flaps 36 for clarity of illustration of the fusion bonds 44. It is understood, however, that the apertures 29 will ordinarily at least be distributed over the main body portion (or "central absorbent pad") 21 of the sanitary napkin 20.

The topsheet 28 preferably has a caliper of between about 0.001–0.002 inches (0.025–0.05 mm) prior to any aperturing. The topsheet 28 preferably has a greater caliper (of between about 0.02–0.03 inches) after aperturing. This is due to the formation of the tapered capillary structures (shown in FIG. 7) created when the topsheet is formed according to several of the processes described herein.

Figure 16:
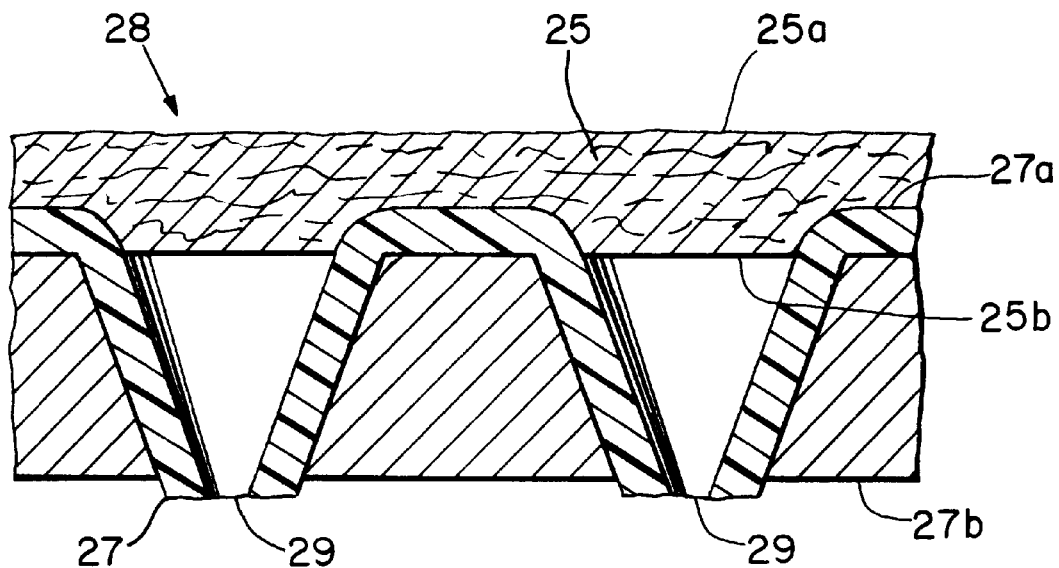
FIG. 16 is an edge view of an alternative topsheet that comprises a nonwoven material and a formed film.

Suitable formed films are described in U.S. Pat. No. 3,929,135 issued to Thompson on Dec. 30, 1975, U.S. Pat. No. 4,324,426 issued to Mullane et al. on Apr. 13, 1982, U.S. Pat. No. 4,342,314 issued to Radel et al. on Aug. 3, 1982, U.S. Pat. No. 4,463,045 issued to Ahr, et al. on Jul. 31, 1984, and U.S. Pat. No. 5,006,394 issued to Baird on Apr. 9, 1991. Additional suitable formed and hydro-formed films are described in U.S. Pat. Nos. 4,609,518, 4,629,643, 4,695,422, 4,772,444, 4,778,644, and 4,839,216 issued to Curro, et al., U.S. Pat. No. 4,637,819 issued to Ouellette, et al. In another embodiment, the topsheet 28 comprises a nonwoven material 25 and a plastic film 27 shown in FIG. 16 and described in greater detail in U.S. patent application Ser. No. 07/794, 745 filed by Aziz, et al. on Nov. 19, 1991. Still other materials suitable for use as a topsheet are described in U.S. Pat. No. 4,775,579 issued to Hagy, et al. on Oct. 4, 1988, U.S. Pat. No. 5,023,124 issued to Kobayashi on Jun. 11, 1991 and in European Patent Application 0 304 617 A2 published Mar. 1, 1989 in the name of Suda, et al.

Figure 7:
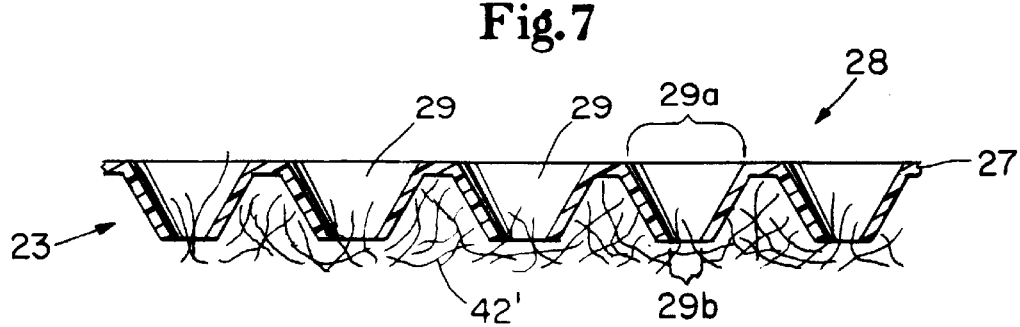
FIGS. 7 and 7A are a simplified schematic view and a greatly enlarged bottom plan view photograph of a topsheet material which comprises an apertured film with entangled nonwoven fibers.

In one particularly preferred embodiment, the topsheet 28 comprises fiber-entangled film. The term "fiber-entangled film" refers to apertured films having fibers entangled in and around their apertures. The apertured film of such a topsheet could comprise any of the films or scrims described above. The film has nonwoven fibers loosely mechanically or thermo-mechanically entangled therewith. The fibers are preferably entangled along or from the direction of the core-facing side 28b. FIG. 7 shows an example of such a fiber-entangled topsheet material. FIG. 7 shows a topsheet 28 created by attaching hydrophilic (or hydrophobic) fibers 42' to an apertured film. The fibers 42' used could be of any polyolefin nature. The fibers 42' can be used in conjunction with the acquisition layer 34, or to replace the acquisition layer 34.

The primary objective of entangling the fibers is to drain the plastic film of any surface fluids. More specifically, the entangled fibers 42' are in much closer contact with the bottom opening 29b of the apertures 29 than is possible by simply placing a nonwoven material adjacent the film. This close contact prevents any gaps from forming between the nonwoven and the film at the bottom opening 29b. The elimination of gaps allows the fibers 42' to drain liquids through the film 27 and prevents a meniscus from forming at the bottom opening 29b. Otherwise, liquids may pool at this location and subsequently rewet the wearer's skin.

The fibers could be mechanically or thermo-mechanically entangled with the film by any suitable process. For instance, the fibers could be meltblown onto the film, spunbonded onto the film, carded onto the film, thermo-mechanically entangled with the film such as being flocked or meltblown on the plastic film while the film is still in its molten state, or hydro-entangled with the film.

Figure 18:
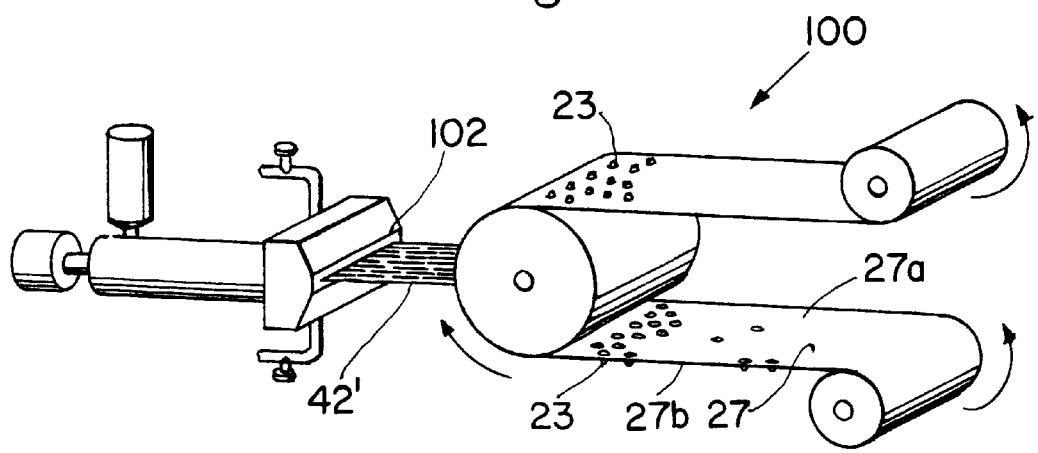
FIG. 18 is a simplified schematic view of one process that could be used to make the topsheet shown in FIGS. 7 and 7A.
Figure 19:
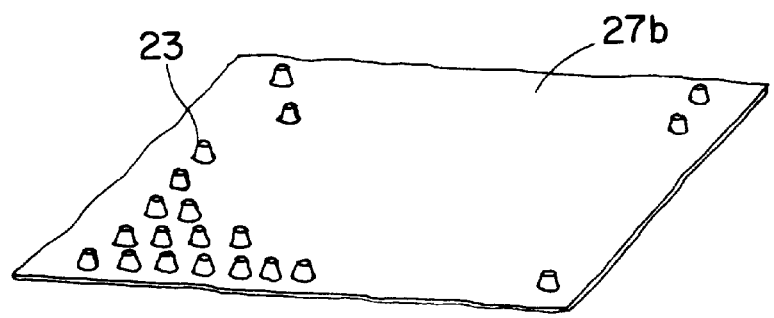
FIG. 19 is a perspective view of the formed film supplied to the process shown in FIG. 18.

The preferred method for attaching fibers to the film is via a process that uses either air attentuation or mechanical drawing combined with air lay-down. FIG. 18 shows a preferred way of obtaining such topsheet structure. In this case, a synthetic thermoplastic polymeric hydrophilic material is extruded in the form of a fiber. The fibers are subjected to attenuation by directing a stream of air on the fibers once they exit the die 102. This process is known as a meltblowing process and is disclosed in Exxon patent U.S. Pat. No. 3,978,185 to Buntin, et al. Suitable hydrophilic fibers may be formed from, intrinsically wettable fibers such as nylon co-polymers comprising a nylon component and a hydrophilizing component. Such a material is commercially available from Allied Signal Inc. under the trade designation Hydrofil SCFX. The core-facing 27b side of the film 27 should be facing the meltblowing die 102 head. The film 27 preferably has a multiplicity of cone-like projections (or "cones") 23 which define tapered capillaries. The processes of making this type of film 27 may form cones 23 that have outside surfaces that form shredded or jagged edges. One particularly suitable apertured film 27 is disclosed in U.S. Pat. No. 4,463,045 and ring-rolled as described below to provide it with a degree of extensibility.

Figure 7A:
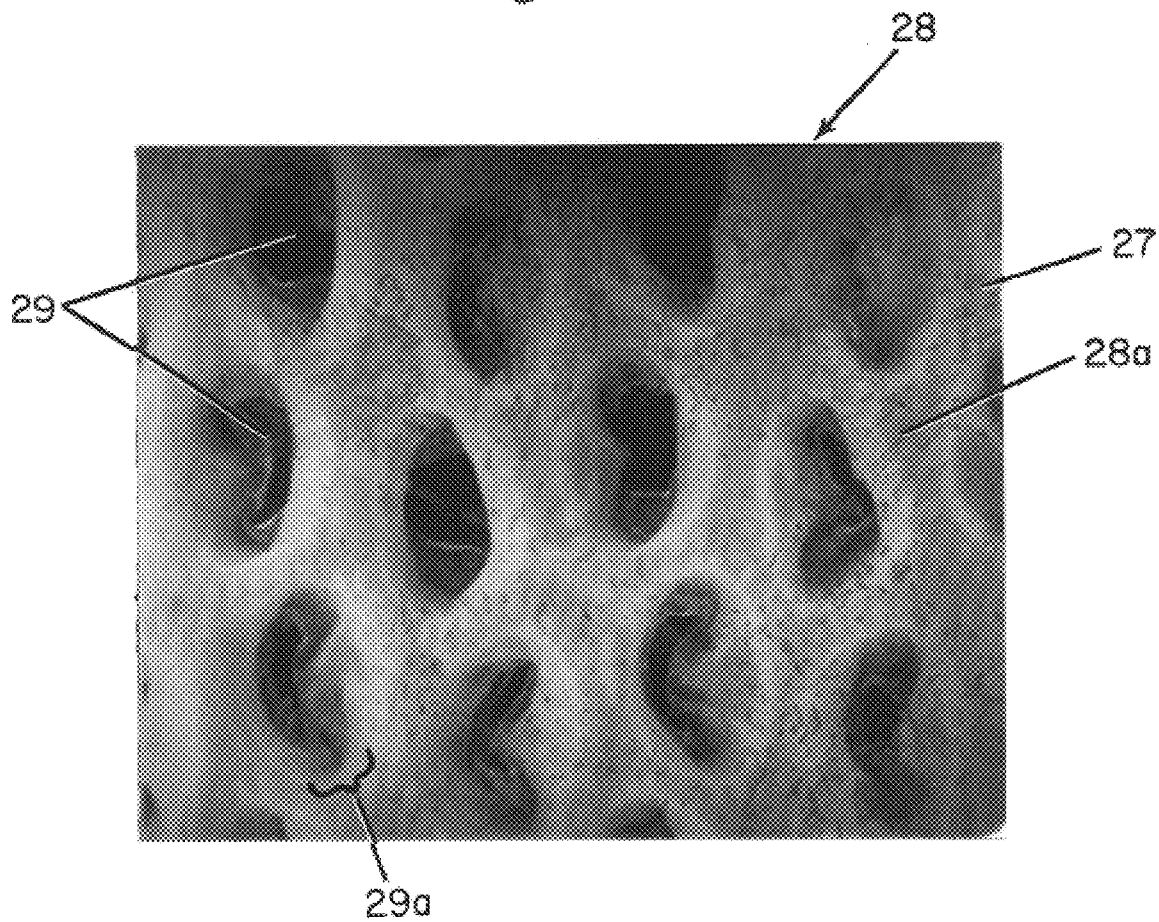

The fibers 42' are ejected from the die 102 and attach to the core-facing side 27b of the plastic film 27. The molten fibers 42' and the cones 23 of the film 27 tend to melt and fuse. This causes the fibers 42' to permanently attach to the film as shown in FIG. 7A. It is believed that the attachment occurs primarily between the partially molten fibers 42' and the partially shredded edges formed on the outside surfaces of the cones 23 that form of the capillaries of the apertured film 27.

In another preferred embodiment the fibers 42' are of a thermoplastic synthetic nature but hydrophobic. Hydrophobic fibers such as polyethylene can be available from the Dow Chemical Company under the trade designation ASPUN, or as polypropylene from the Exxon Corporation under the trade name ESCORENE 3,400 and 3,500 series. Once formed, the entire web is treated by any known methods (described in greater detail below) to render it hydrophilic. Such process will allow the apertures to better handle fluid. It is also possible to ring-roll the entire web after these treatment processes.

The fiber-entangled topsheet 28 material provides more intimate contact between the apertured film 27 and the nonwoven fibers 42'. This can create advantages of improved liquid transport through the film to the fibers 42' and the underlying layers such as the absorbent core 32 or the acquisition layer 34. It may also provide improved comfort since the film 27 will be less likely to separate from the underlying entangled fibers 42'. This will prevent the topsheet 28 from moving into the crevices of the wearer's body.

In still another preferred embodiment (shown in FIG. 15), the sanitary napkin 20 is comprised of components that are extensible (i.e., capable of stretching, particularly in the longitudinal direction) when the sanitary napkin is worn. Preferably, the sanitary napkin 20 is capable of elongating between about 15% and about 40% of its unstretched length. This extensibility provides better in-use fit, attachment to the wearer's undergarments, comfort, and decreased staining. In other embodiments, only limited portions of the components of the sanitary napkin 20 need be capable of stretching.

Figure 15:
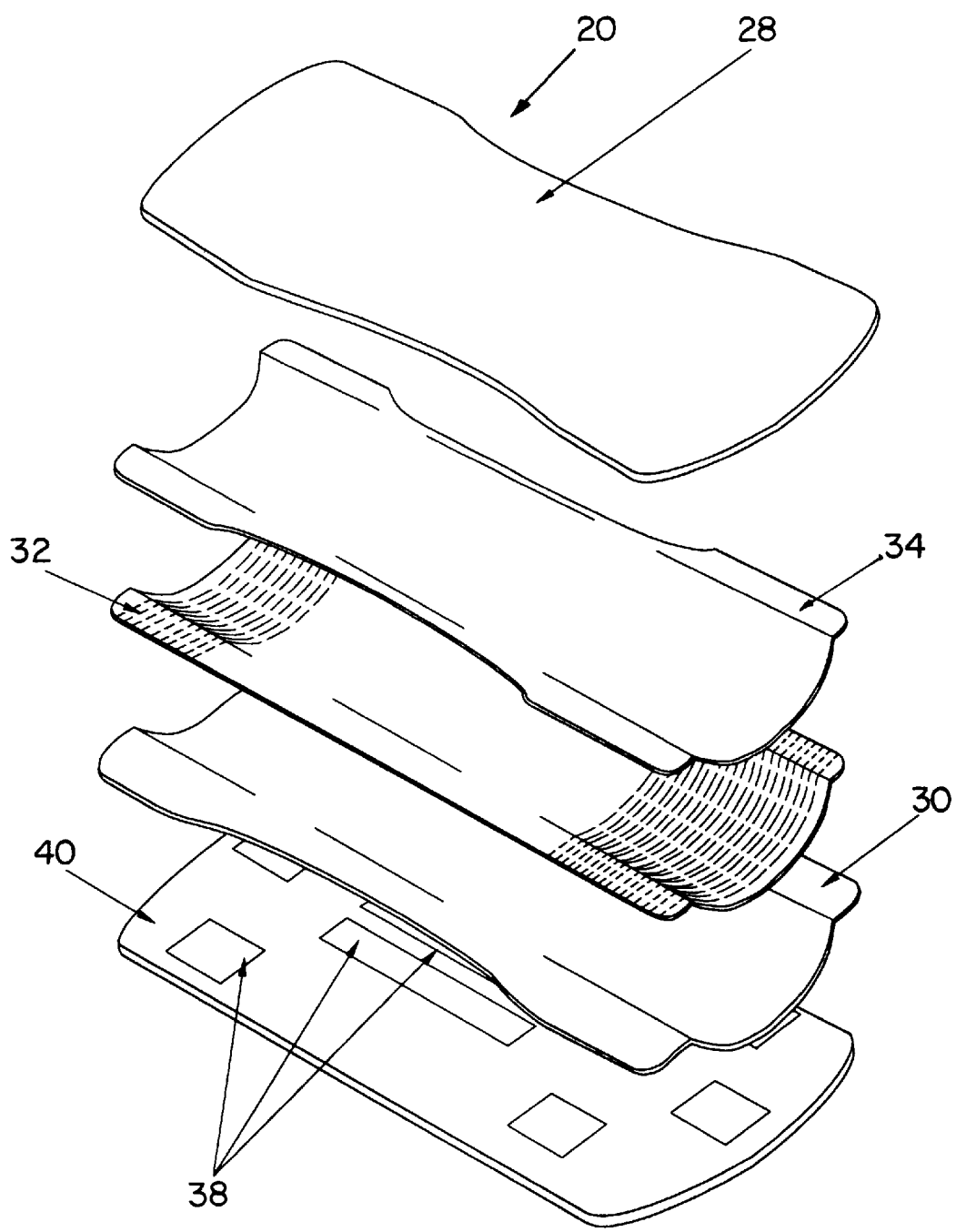
FIG. 15 is an exploded perspective view showing the assembly of a sanitary napkin which contains a preferred absorbent core and panty fastening adhesive for use in the present invention.

One type of topsheet 28 for use in the embodiment shown in FIG. 15 can be made in accordance with U.S. Pat. No. 4,463,045 and ring rolled to provide it with a degree of longitudinal extensibility. Suitable processes for ring rolling or "pre-corrugating" are described in U.S. Pat. No. 4,107,364 issued to Sisson on Aug. 15, 1978, U.S. Pat. No. 4,834,741 issued to Sabee on May 30, 1989 and in co-pending, commonly assigned U.S. patent application Ser. Nos. 07/662,536 filed by Gerald M. Weber et al., 07/662,537 filed by Kenneth B. Buell et al. and 07/662,543 filed by Gerald M. Weber et al. on Feb. 28, 1991, all filed Feb. 28, 1991. The fold lines in the corrugations of the topsheet should run in the transverse direction so the topsheet is longitudinally extensible. Such a topsheet is described in greater detail in the following U.S. patent applications which were filed on Jun. 23, 1991: Ser. No. 07/734,404 filed in the names of Thompson, et al.; U.S. patent application Ser. No. 07/734,392 filed in the names of Thompson, et al.; and, Ser. No. 07/734,405 filed in the names of Buenger, et al. These latter three patent applications may be referred to collectively as the "Capillary Channel Fiber" patent applications.

In addition, in preferred embodiments of the present invention, at least a portion of the topsheet 28 is treated with a surfactant. This can be accomplished by any of the common techniques well known to those skilled in the art. Suitable methods for treating the topsheet with a surfactant are described in a number of references, including U.S. Pat. Nos. 4,950,264 and 5,009,653 issued to Osborn, and in U.S. patent application Ser. No. 07/794,745 filed by Aziz, et al. on Nov. 19, 1991. The latter patent application teaches treating the apertured film component of a nonwoven/apertured thermoplastic formed film topsheet with a surfactant. The surfactant is preferably incorporated into the resin used to make the thermoplastic formed film.

Treating the topsheet 28 with a surfactant renders the surface of the topsheet 28 more hydrophilic. This results in liquid penetrating the topsheet 28 faster than it would if the surface were not treated. This diminishes the likelihood that body fluids will flow off topsheet 28 rather than being drained through the topsheet 28.

B. The Acquisition Layer

The acquisition layer (or "acquisition/distribution layer", or acquisition sheet") 34 is shown in FIG. 2. It is positioned between the topsheet 28 and (at least a portion of) the absorbent core 32.

In the embodiment shown in FIG. 2, the acquisition layer 34 is a folded sheet of nonwoven material. It should be understood, however, that the acquisition layer 34 need not be a folded sheet. The terms "layer" or "web", as used herein, include, but are not limited to single unfolded sheets, folded sheets, strips of material, loose or bonded fibers, multiple layers or laminates of material, or other combinations of such materials. These two terms are thus, not limited to single unfolded layers or sheets of material.

In FIG. 2, the acquisition layer 34 is a "double" z-folded sheet. The sheet 34, is more specifically folded so that when the sanitary napkin is cut along the transverse line, the left half of the folded sheet appears as a reverse "z" in cross section and the right half appears as a "z". The sheet 34 is preferably folded so that it has an upper portion 54 that appears as a rectangular strip in plan view. The upper portion 54 of the acquisition layer 34 is preferably about 227 mm long, and between about 25 and about 38 mm wide. The upper portion 54 preferably has a caliper of from about 0.5 mm up to about 4 mm (the higher end of this range creates thicker products). Such a folded arrangement is described in greater detail in U.S. patent application Ser. No. 07/605,583 filed on Oct. 29, 1990 in the name of Visscher, et al.

Figure 3:
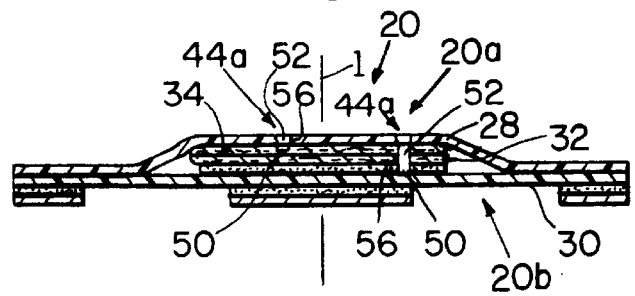
FIG. 3 is a simplified transverse cross-sectional view similar to that of FIG. 2, showing an alternative arrangement of the components of the sanitary napkin.

FIG. 3 is a simplified cross-sectional view similar to that of FIG. 2, showing an alternative arrangement of the components of the sanitary napkin 20. In FIG. 3, rather than being a separate layer that is located on top of the core 32, the acquisition layer 34 is an integral layer (or component) that comprises the top layer of a laminated absorbent core 32 structure.

In still other alternative embodiments, the acquisition layer 34 may be omitted entirely. In embodiments without an acquisition layer 34, the absorbent core 32 should be comprised of at least some types of fibers (preferably synthetic fibers) that the topsheet 28 can be fused to. A sufficient amount of these fibers are preferably located near the body-facing surface 32a of the absorbent core 32 to facilitate the fusion.

It is possible to create a bond with natural fibers, such as cellulose by melting a film topsheet around cellulose fibers. Better bonds are typically formed with synthetic fibers, however. Cellulose fibers are rather short. When the fusion bonds are spaced apart, some cellulose fibers may be unbonded or only bonded in one place. This can result in these fibers pulling loose from the bonded structure. Synthetic fibers can be made longer than cellulose fibers.

The topsheet 28 is generally described herein as being fused to the acquisition layer 34. This has been done for simplicity of description. (It is easier to discuss one preferred embodiment then it is to simultaneously describe all possible embodiments.) The topsheet 28 may be fused directly (or indirectly) to (one or more) other underlying components. In the broadest sense, the topsheet 28 comprises a first component that is fused to an underlying second component. The second component may be a separate component. Alternatively, the second component could be part of another component, such as part of the topsheet, part of the core, or part of some other component.

Thus, for example, it is understood that in embodiments where the acquisition layer 34 is an integral layer of the core 32 (such as that shown in FIG. 3) or omitted entirely, the topsheet 28 may be considered to be fused to part of the absorbent core 32.

The function of the acquisition layer 34 is generally described in relation to the absorbent core 32. It is understood that in embodiments in which the acquisition layer 34 comprises part of the core 32, the acquisition layer 34 will function in much the same way. However, it will function in the same way with respect to the remaining portions of the core 32 (rather than with the core per se).

The acquisition layer 34 serves to improve wicking of exudates over and into the absorbent core 32. There are several reasons why the improved wicking of exudates is important. This provides a more even distribution of the exudates throughout the absorbent core.

The improved wicking also allows the sanitary napkin 20 of the present invention to be made relatively thin. The acquisition layer 34 is capable of dispersing exudates over a large surface area of the absorbent core 32. The acquisition layer 34 thus allows the sanitary napkin 20 to absorb relatively large amounts of exudates. The bulky prior art sanitary napkins relied on a high degree of vertical absorption at the point where exudates are initially deposited. Because the absorbent cores of these prior napkins were fairly thick, they could absorb a large volume of exudates while utilizing only a small degree of the surface area or lateral absorption capacity. The sanitary napkins 20 of the present invention may absorb relatively large amounts of exudates because the wicking disperses the exudates over a large surface area of the absorbent core 32 where the exudates can better and faster be vertically absorbed into the absorbent core 32.

The acquisition layer 34 may have sufficient open spaces between its fibers to provide a fairly high degree of temporary liquid holding capacity. Temporary holding capacity is useful during the time interval between the time exudates are deposited onto the topsheet 28 and the time they are absorbed by the absorbent core 32. This is particularly useful in diapers and incontinent articles. This allows the acquisition layer 34 to acquire and temporarily hold gushes of liquids (such as urine) in cases where the core 32 absorbs liquids at a slower rate than they are deposited onto the absorbent article.

The acquisition layer 34 may also be used to direct exudates toward the ends of the core 32d. Liquid exudates that are deposited on the core 32 will tend to be distributed radially outward from the place where they are deposited. Since the core 32 of the sanitary napkin 20 is relatively narrow in comparison to its length, liquid exudates will reach the longitudinal edges 32c of the core 32c much sooner than they will reach the ends 32d of the absorbent core. The acquisition layer 34 can be used to longitudinally wick and direct exudates toward the ends 32d of the core 32. This more effectively utilizes the capacity of the core, and reduces the possibility of leakage caused by exudates prematurely reaching the longitudinal edges 32c of the core.

The wicking referred to herein may (unless otherwise stated) encompass the transportation of liquids in both the "x-y" plane and in the z-direction. These directions are shown in FIGS. 1 and 2. The acquisition layer 34 preferably transports liquids well in both directions.

Ideally, liquids are transported in a pyramidal distribution pattern (or perhaps more accurately, a conical distribution pattern). The apex of the pyramid (or the cone) is the point where the liquid is deposited on the body-facing surface 34a of the acquisition layer 34. The liquids are then distributed down and outward to the base of the pyramid (or cone).

In one preferred embodiment, liquids are distributed to the core 32 by a cascading action. This type of distribution is described in greater detail in U.S. patent application Ser.

Nos. 07/637,090 and 07/637,571 filed by Noel, et al. and Feist, et al. It can be thought of as being analogous to the filling of an ice cube tray with water. Liquids are distributed so that after one section of the core 32 reaches capacity, liquids flow laterally then downward to fill up adjacent sections of the core 32.

The combination of the acquisition layer 34 and the topsheet 28 also provides the sanitary napkin with the enhanced gush acquisition and enhanced wipe acquisition described in greater detail in U.S. Pat. Nos. 4,950,264 and 5,009,653 issued to Osborn. (Thus, the acquisition layer 34 may be referred to as a "wipe acquisition sheet".)

The characteristics of the acquisition layer 34 are as follows. The acquisition layer 34 should be liquid permeable. The acquisition layer 34 is also preferably compliant, soft feeling, and non-irritating to the user's skin. It can be made from any materials that are capable of dispersing exudates as described above. The materials are preferably also capable of having the topsheet 28 fused to them. The acquisition layer 34 may also be provided with stretch properties. The acquisition layer 34 has a body-facing face (or side) 34a, and a garment-facing face 34b.

The acquisition layer 34 should be hydrophilic. The fibers or yarns 42 comprising the acquisition layer 34 may be inherently hydrophilic. Alternatively, they may be treated to render them hydrophilic. Suitable methods for rendering fibers hydrophilic include treating them with a surfactant. The fibers can be treated by spraying the material comprising the acquisition layer with a surfactant or immersing the material into the surfactant. A more detailed discussion of such a treatment and hydrophilicity is contained in U.S. Pat. Nos. 4,988,344 and 4,988,345 issued to Reising, et al. and to Reising, respectively. The hydrophilicity of these fibers allows the acquisition layer 34 to draw liquid exudates through the topsheet 28 from below.

The acquisition layer 34 may be comprised of woven or nonwoven materials. These materials may be synthetic, or partially synthetic and partially natural materials. Suitable synthetic fibers include polyester, polypropylene, polyethylene, nylon, viscous rayon fibers, or cellulose acetate, with polyester fibers being preferred. Suitable natural fibers include cotton, cellulose, or other natural fibers. The acquisition layer 34 may also be at least partially comprised of cross-linked cellulose fibers. Suitable cross-linked cellulose fibers are described in U.S. Pat. No. 4,888,093, issued Dec. 19, 1989 to Cook, et al.; U.S. Pat. No. 4,822,543, issued Apr. 18, 1989 to Dean, et al.; U.S. Pat. No. 4,889,595, issued Dec. 26, 1989 to Schoggen, et al.; U.S. Pat. No. 4,898,642, issued Feb. 6, 1990 to Moore, et al.; and U.S. Pat. No. 4,935,022 issued Jun. 19, 1990 to Lash et al. The quantity of such natural or modified fibers, however, should not be so great that the topsheet 28 cannot be adequately fused to the remaining synthetic fibers. The acquisition layer 34 may also be comprised of capillary channel fibers (that is, fibers having channels formed therein, preferably, on their exterior surfaces). Such fibers are described in greater detail in EPO Patent Application 0 391,814 published Oct. 10, 1990, and in the Capillary Channel Fiber patent applications. The acquisition layer 34 can also be comprised of combinations of the above materials, such as blends of fibers similar to those described below for use in the absorbent core, or any equivalent material or combinations of materials.

The material comprising the acquisition layer 34 may have melting temperatures in different embodiments that are less than, equal to, or greater than that of the topsheet 28. The material comprising the acquisition layer 34 preferably has a melting temperature that is greater than or equal to that of the material comprising the topsheet 28. Polyester fibers are preferred because they have a high melting temperature (between about 375° and about 400° F.). This quality makes them especially well-suited to spunlace processing. Spunlace processing utilizes a high temperature drying process. Polyester fibers are able to undergo spunlacing processes without being damaged.

The use of polyester fibers also has the advantage that such fibers are particularly suitable for use with the preferred types of topsheet materials. Polyester fibers will not melt at the typical melting temperature of the topsheet when the topsheet 28 is fused to the acquisition layer 34. This has the advantage that the fibers 42 will remain in their fibrous form after fusion. If the topsheet 28 comprises a polyethylene formed film, for example, it may have a melting temperature in the range of between about 165 and about 215° F. The present invention, thus, advantageously uses materials with dissimilar melting temperatures (as described below) to create structures that improve the acquisition through such layers after they are fused.

The fibers or yarns 42 comprising the acquisition layer 34 may be of any length, from staple length to continuous filaments. The length of the fibers 42 is preferably between about 1 inch and about 3 inches (between about 2.5 cm. and about 7.5 cm.), and most preferably is about 1.5 inches (about 3.8 cm.). The fibers 42 preferably have a denier per filament of between about 1 and about 3, most preferably about 1.5.

The fibers 42 of the acquisition layer 34 are preferably oriented primarily in a single direction. Typically, the acquisition layer 34 can be manufactured with its fibers oriented in the machine direction (MD). The acquisition layer 34 can be placed in the product with most of the fibers 42 oriented in the longitudinal direction. (That is, the fibers 42 are generally parallel to the longitudinal centerline 1 of the sanitary napkin 20). The phrase "generally parallel" to the longitudinal centerline (and similar phrases) as used herein, is intended to include fibers that angle away from the longitudinal centerline. These fibers are considered to be generally parallel as long as they are oriented more in the longitudinal direction than the transverse direction. The orientation of the fibers 42 of the acquisition layer 34 causes liquid exudates deposited on the acquisition layer 34 to preferentially wick and be distributed toward the ends 32d of the absorbent core 32.

The acquisition layer 34 may be any suitable size. The acquisition layer 34 need not extend the full width of the absorbent core 32. The acquisition layer 34 could, for instance, be in the form of a strip positioned similarly to (and of a size similar to) the upper portion 54 of the z-folded sheet shown in FIGS. 1 and 2.

The acquisition layer 34, if nonwoven, can be made by a number of different processes. These include, but are not limited to the following in order of preference from least to most preferred: meltblown, spunbonded, carded, the latter including, in order of preference, thermally-bonded, air-through bonded, powder bonded, latex bonded, solvent bonded, or most preferably, spunlaced. The latter processes are more preferred because it is easier to orient the fibers in a single direction in such processes.

Suitable commercially available products for use as the acquisition layer 34 include a 70%/30% rayon/polyester fabric known as SONTARA. The SONTARA fabric is described in greater detail in U.S. Pat. Nos. 4,950,264 and 5,009,653 issued to Osborn.

In a particularly preferred embodiment, the acquisition layer 34 comprises a spunlace nonwoven web comprised of permanently wettable fibers. Preferably, the acquisition layer 34 is a 30 g/yard2 (35 g/m²) polyethylene theraphtalate (or PET) spunlace nonwoven web. Spunlaced fabrics of this type are manufactured by the Veratec Company of Walpole, Mass. The spunlace nonwoven web is formed in such a way that most of the fibers are oriented in a single direction.

The fibers of this particularly preferred acquisition layer 34 material are made of a PET resin and are coated with a proprietary permanently wettable finish known as CELWET. These fibers are available from the Hoechst Celanese Corporation of Charlotte, N.C. The term "permanently wettable", as used herein, refers to fibers that will sink in less than or equal to about 7 seconds when tested according to the ASTM D 1117-74 Basket Sink Method. The CELWET finish is particularly preferred for use in sanitary napkins having a topsheet 28 comprising an apertured film or scrim with hydro-entangled nonwoven fibers because fibers coated with it remain extremely hydrophilic after hydro-entangling processes, and therefore, wick blood very well.

(1) Fusion of the Topsheet to the Acquisition Layer

The topsheet 28 is secured in contact with an underlying layer. The underlying layer should either have some absorptive capacity, or be capable of transporting liquids to a layer with absorptive capacity. In the preferred embodiment shown in FIG. 2, this is the acquisition layer 34. This relationship results in liquid penetrating topsheet 28 faster. In conventional products, the topsheet 28 is initially maintained in contact with the underlying layer by applying adhesive between the underlying layer and the topsheet 28.

In the present invention, the topsheet 28 is preferably joined in a face-to-face relationship with the underlying acquisition layer 34 by fusion bonding the topsheet 28 and the acquisition layer 34. The fusion of the faces of the topsheet 28 and the acquisition layer 34 of interest to the present invention is located on those portions of the respective faces that are inboard of any liquid impervious seam, such as around the periphery 26 of the sanitary napkin 20. (The term "inboard" means toward the intersection of the longitudinal and transverse centerlines.)

The term "fusion bonding", as used herein, is intended to include, but not be limited to: (1) true fusion in which both fused materials are melted together; as well as (2) attachments in which a first material is melted and the melting causes the first material to become attached to a second unmelted material by mechanical attachment.

The topsheet 28 and the acquisition layer 34 can be secured entirely by fusion bonding, or partially by fusion bonding and partially by other types of attachment means. The fusion can be accomplished by heat and/or pressure bonds, ultrasonic bonds, dynamic mechanical bonds, and the like. Pressure can be applied in any suitable manner, such as by moving the two components between counter-rotating rolls, placing the materials on an anvil and forcing a platen down on the materials, applying vacuum pressure, and the like.

Suitable means that can be adapted for use in fusing the topsheet 28 to the acquisition layer 34 are described in at least some of the following patents: U.S. Pat. No. 4,430,148 Schaefer, U.S. Pat. No. 4,515,595 Kievit, et al., U.S. Pat. No. 4,531,999 Persson, et al., U.S. Pat. Nos. 4,710,189 and 4,808,252 issued to Lash, U.S. Pat. No. 4,823,783 Willhite, Jr., et al. and U.S. Pat. Nos. 4,854,984 and 4,919,756 issued to Ball, et al.

The two bonded layers, the topsheet 28 and the underlying acquisition layer 34, should preferably display an average peel strength of greater than or equal to about 50 g/inch, more preferably, greater than or equal to about 65 g/inch measured on a 1 inch×6 inch (2.5 cm×15 cm.) sample. These values are obtained by measurements made according to the 180° Peel Bond Strength Test described in Section 4 below entitled "Test Methods". It is recognized, however, that these are preferred values. There may be embodiments in which lesser bond strengths may be used (for instance, if the acquisition layer 34 is also partially mechanically entangled with the topsheet 28).

The fusion bonding preferably comprises a pattern of individual fusion bonds 44. The individual bonds 44 can be of any plan view shape. For instance, the bonds 44 can be in the form of straight or curved lines, geometric shapes such as circles, squares, rectangles, diamonds, and the like, or irregular shapes. The bonds 44 can be arranged in many different manners.

FIG. 1 shows one particularly preferred bonding pattern. The fusion bonds 44 comprise discrete points of attachment which comprise circular bonds. The bonds 44 are arranged in a pattern that is preferably distributed over the entire body surface 20a of the sanitary napkin, less the flaps. (This is the portion of the sanitary napkin previously referred to as the "main body portion" 21.) The bonding pattern shown in FIG. 1 comprises a plurality of larger bonds 44a and a plurality of small bonds 44b. The large bonds 44a are positioned in the longitudinal central region 46 of the sanitary napkin. The smaller bonds 44b are positioned in the longitudinal side regions 48 of the sanitary napkin.

In FIGS. 1 and 2, the large bonds 44a have a diameter of about 2 millimeters. The large bonds 44a preferably form a bonded area of about 4 mm². The small bonds 44b have a diameter of about 0.5 millimeter. The small bonds 44b preferably form a bonded area of about 0.25 mm². The diameter of the bonds 44 in this bond pattern can range from about 0.5 millimeter to about 3 millimeters. The diameter of the bonds 44 preferably ranges between about 0.5 mm. and about 2 mm. The bonds 44 are typically larger than the apertures 29 in the topsheet 28. The bonds 44 form bonded areas 52 (which are described in greater detail below in conjunction with FIG. 8) that preferably have a range of depths of between about 0.5 mm. and about 1.5 mm, and more preferably, between about 1 mm. and about 1.5 mm. (Thus, in the case of the z-folded acquisition layer 34, the larger bonds 44a penetrate the topsheet and only part of the caliper of upper portion 54 of the folded sheet that forms the acquisition layer 34.)

The bonds 44 are preferably in the form of a plurality of spaced apart diagonal lines. The lines of the preferred bonding pattern shown run in the same direction in the longitudinal central region 46 and the longitudinal side regions 48. The bonds 44 are preferably spaced between about 5 mm. and about 16 mm. apart, more preferably between about 5 mm. and about 8 mm. apart. This spacing is measured in the direction of the shortest distance between the bonds. The large bonds 44a are preferably distributed in a density of 18 bonds per square inch. The small bonds 44b are preferably distributed in a density of 25 bonds per square inch. It should be understood, however, that the bonding pattern shown is a preferred pattern, and that many other patterns are also suitable.

The bonds 44 are typically spaced further apart than the apertures 29 in the topsheet 28. Thus, the bonds 44 will occasionally be formed over one or more apertures 29, or parts of apertures 29. There is no need to attempt to align the bonds 44 and the apertures 29, however, because the bonds 44 do not interfere with the flow of exudates to the underlying layers.

The strength of the individual bonds 44 determines the strength of the bond between the layers. Typically, the strength of the bond is related to the area of the bond (i.e., the larger the area of the individual bond 44, the stronger the bond). A plurality of closely spaced weaker bonds may provide a large overall bonded area. However, the bonded layers will typically separate by applying the relatively low peel force required to separate each weaker bond. Further, if the bonds are too close together, the effect of the bonding will approach that created when using adhesives and a stiffer product will result. The present invention has the advantage that larger and generally stronger bonds can be used without interfering with acquisition of liquids. The present invention is believed to overcome the limitations that prevented larger bonds from effectively being used. This aspect of the invention, thus, avoids the undesirable problems caused by using closely-spaced small bonds.

FIG. 8 is a close up schematic side view of a bond site. (The bond site shown is a greatly enlarged schematic view of the bond 44a shown to the left of the longitudinal centerline 1 in FIG. 3.) The melting of the film topsheet 28 to the fibers 42 of the acquisition layer 34 as noted above, leaves the fibers 42 intact. FIGS. 9 and 10 show this feature. The bond site comprises a fused area (or bonded area) 50 where the topsheet 28 is melted to the fibers 42 of the acquisition layer 34. The regions of the topsheet 28 and acquisition layer 34 surrounding the bond site define a bond aperture 52 (an aperture formed by the bond). The bond aperture 52, because it is within the range of depths specified above, penetrates the topsheet 28 and a portion of the caliper of the acquisition layer 34.

As FIG. 8 illustrates, when the faces of the topsheet 28 and the underlying layer are described herein as being fused, it is understood that this refers to the overall relationship between these components. The components may be considered to be held together at their faces even though the bonds 44 may, and likely, will penetrate the face of the underlying layer at the interface between the topsheet 28 and the underlying layer.

The bonding forms a sink or reservoir structure which is bounded at the bottom by the fused area 50. In FIG. 8, the sides 56 of the reservoir are formed partially by portions of the film topsheet 28 and partially by portions of the acquisition layer 34. The acquisition layer 34 is comprised of a plurality of fibers 42 with a plurality of open spaces (or void spaces) 58, between the fibers 42. The open spaces and the hydrophilic fibers of the acquisition layer 34, thus, provide a plurality of drainage passageways or drains 60 leading away from the reservoir. The drains 60 described above are located along the lower portion of the sides 56 of the reservoir around the periphery of the fused area 50.

In other embodiments, the sides 56 of the reservoir may be formed by different components. The bond 44a to the right of the longitudinal centerline 1 in FIG. 3 shows an example of such a case. This bond 44a is formed all the way through the various components of the sanitary napkin 20 (other than the backsheet 30). The drains 60 leading away from the reservoir formed by this bond may be formed by portions of any of the different components or layers of the sanitary napkin 20 that the bond aperture 52 passes through.

It is understood that the bonds 44 described herein may be formed deep enough to go into part or all of any of the various components or layers of the sanitary napkin 20 as long as certain requirements are met. Preferably, as in the case of the first bond embodiment described above, the fused area 50 is located below the core-facing face 28b of the topsheet 28. This provides a bond structure that will not interfere with drainage to the underlying layers. The bonding should also preferably produce side walls 56 that are open into at least some of the layers beneath the topsheet 28. The side walls 56 formed by the layers that lie beneath the topsheet 28 need not all be open, however. For instance, every other layer, etc. could have side walls 56 that are sealed off.

The bonding should not produce side walls 56 that seal off any underlying layers that are supposed to remain open for transportation of liquids. This can be accomplished if the material(s) comprising these underlying layers have melting temperatures which are greater than that of the topsheet 28 material (or other layers to which they are fused). The material(s) comprising these layers must also have melting temperatures greater than that created in the fusion process. A final requirement is that the bonding should not create an aperture completely through any lower layer, such as the backsheet 30, that is intended to be liquid impervious.

It is also possible that the drains 60 could be formed by structures other than the void spaces in adjacent layers. This may cause the drains 60 to be in locations other than those portions of the acquisition layer 34 that are located above the periphery of the fused area 50. For instance, as shown in FIG. 8, the drains 60 could also be formed in the fused area 50. The drains 60 could be formed by cracks 70 in the fused area 50 at the bottom of the reservoir structure.

In other embodiments, holes 72 could be intentionally formed in the fused area 50. For instance, a device 74 used to create the fusion bonds 44 is shown in FIG. 8A. The device 74 (part of which is shown) could have a head 76 equipped with one or more piercing elements 78 extending from its bonding surface 80. When the bond 44 is formed, the bonding surface 80 will form the fused area 50. The piercing elements 78 are used to leave holes 72 in the fused area sufficient to form drains 60. It is even possible that the piercing elements could pierce and/or break some of the fibers 42 of the underlying layer. This embodiment is significant in that it may provide a bond structure which is an exception to the general preference (described below) for deeper bonds. This structure will allow the transportation of liquids to underlying layers even though the bond 44 may be a relatively shallow bond that has a fused area 50 at the interface between the bonded layers.

Figure 11:
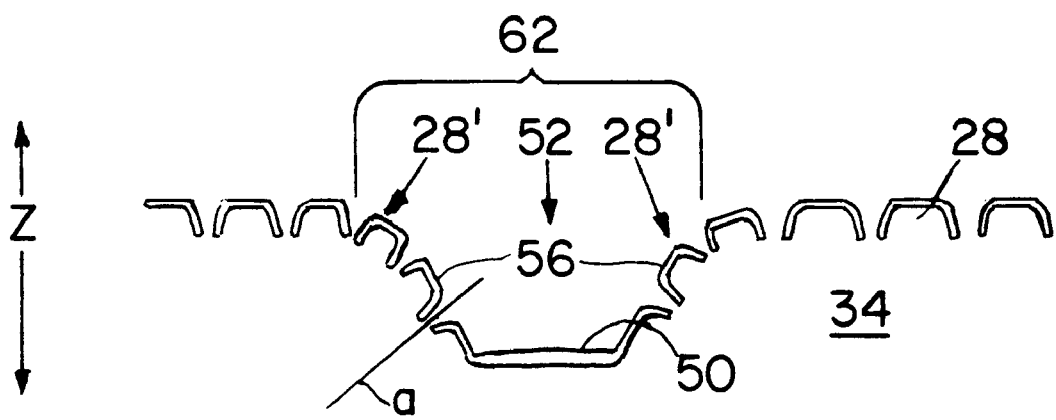
FIGS. 11 and 12 are simplified schematic views showing the difference between the disposition of the topsheet when relatively deep and relatively shallow bonds are used.

In another example, shown in FIG. 11 (and described in greater detail below), the apertures 29 in the topsheet 28 (or portion(s) of the apertures 29) could provide the drains 60 into the underlying layer. As shown in FIG. 11, the sides 56 of the reservoir could be formed entirely by portions of the topsheet 28.

The absorption of body exudates at the bond sites has been observed as a rather unusual phenomenon. While not wishing to be bound by any particular theory, it is believed that the sanitary napkin 20 functions in the following manner. When liquids are placed on the topsheet 28, some of these liquids will flow into the bond apertures 52. This takes place rather quickly. The liquids may then be held momentarily in the bond apertures 52. This is believed to provide a benefit of removing them from contact with the wearer's skin. After the exudates are held for a short period, they are then suddenly drained into the acquisition layer 34. In other embodiments, the exudates may not be held even temporarily. In these latter embodiments, the exudates will immediately flow through the drains 60 and into the acquisition layer 34.

It is, thus, believed that the fused areas 50 which are formed where the topsheet 28 and acquisition layer 34 are bonded does not affect the passage of the liquids in any undesirable manner. Further, contrary to what one might think, instead of blocking transfer of liquids to the absorbent core 32, sanitary napkins with apertured film topsheets having bonds with larger surface areas (and, thus, larger fused areas) appear to perform no worse than those with small bonds, provided the total bonded area does not become excessive.

Figure 12:
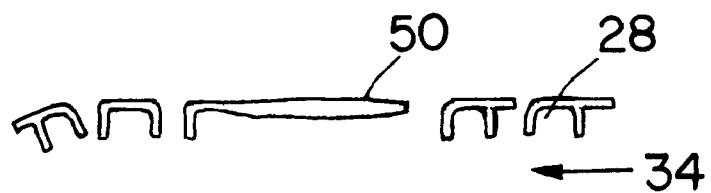

The larger bonded areas 44*a* may, in fact, also create a visual impression of increased absorbency. The larger bonds 44*a* may, thus, be distributed as in the preferred embodiment shown in FIG. 1 to create an impression of increased absorbency in the longitudinal central region 46. The visual impression has been found to be important among consumers because it is often difficult for them to believe a sanitary napkin will perform properly when it is made very thin While not wishing to be bound by any theory, it is also believed that when relatively deep bonds 44 are used the structure formed by the bonding has additional features. FIGS. 11 and 12 show these features schematically. As shown in FIG. 11, the use of deep bonds is believed to cause the portions 28' of the topsheet 28 immediately adjacent the bonded areas 50 to curve in (or cave in) toward the bond aperture. This may have several effects.

The apertures formed by the deep bonds may form a cup-shaped depression. The cup-shaped depression may have a mouth opening 62 that is wider than the bonded area 50 that forms the base of the cup. In other words, the cup structure has tapered side walls 56. This is believed to be caused by the depth and penetration into the nonwoven acquisition layer 34. This stretches the topsheet material 28 over the portions of the nonwoven acquisition layer 34 material surrounding the bonds 44. This cup structure is believed to provide the advantage of good acquisition.

As shown in FIG. 11, the stretching of the topsheet material 28 in the area of the deep bonds 44 may cause the apertures 29 in the topsheet 28 to turn outward to the sides. The apertures 29 have axes designated by reference letter "a". These axes define the alignment of the apertures 29. The axes are ordinarily oriented in the z-direction. When the apertures 29 turn outward, their axes have a horizontal (i.e., x-y direction) component. This orients the apertures 29 toward the adjacent portions of the acquisition layer 34, rather than toward the fused area 50. This may provide the benefit of transfer of liquids through the apertures 29 into the acquisition layer 34.

The structure shown in FIG. 12 provides a contrasting example of a shallow bond 44. The term "shallow bond", as used herein, refers to bonds that penetrate no deeper than the interface between the faces of the two materials when their faces are placed adjacent to each other. The shallow bonds, as shown in FIG. 12, create flat fused areas 50. These flat fused areas 50 are similar to those previously formed when creating an impervious bond around the periphery of a sanitary napkin. The flat fused areas 50 provide no way for liquids to be transmitted into the underlying layer unless they are provided with holes or cracks as described above.

The bonding patterns can be in an infinite number of patterns such as any of a number of different shaped bonds arranged in the form of rows, geometrical shapes, graphical patterns, curved or straight lines, intermittent lines, etc. Further, the pattern or the patterns do not have to be either uniformly distributed, or even in the same pattern over the sanitary napkin. It is also possible that different bonding patterns, etc. could be used between different components of the sanitary napkin 20. For example, the topsheet 28 and the immediately underlying layer could be bonded with one pattern, and the laminate formed thereby could be bonded to another layer using a different bonding pattern.

FIG. 13A shows a bonding pattern in the form of wavy lines. The bonded pattern can even be used to direct liquids from one region of the sanitary napkin to another. For instance, liquids deposited in the area of these wavy lines will tend to flow along and within these lines. In still other alternative embodiments, a quilt pattern could be used to provide the sanitary napkin with a softer feel.

FIGS. 13B–13D show an example of the use of a bond pattern to at least partially aid the sanitary napkin 20 in assuming a particular shape during use. The sanitary napkin 20 shown has a bonding pattern in the form of an oval. This particular bonding pattern is used in conjunction with a flexure-resistant deformation element 82 located on the garment-facing side 20*b* of the sanitary napkin 20*b*. The flexure-resistant deformation element 82 comprises a sheet having ribs 84 and a channel 86 formed therein. Flexure-resistant deformation elements are described in greater detail in European Patent Application publication numbers 0 335 252 and 0 335 253 published Oct. 4, 1989 in the name of Kenneth B. Buell. As shown in FIG. 13D, when the sanitary napkin is subjected to laterally inward oriented compressed forces, it forms a structure of the type described in greater detail in the foregoing European patent applications. Another suitable bonding pattern that may assist in forming a particular structure, might be a pattern in the form of two longitudinally-oriented opposed concave inward lines disposed on opposite sides of the longitudinal centerline 1.

The fusing of the topsheet 28 and acquisition layer 34 may also provide other advantages. For instance, it is believed that using fusion instead of adhesives may increase the overall flexibility of the product. While not wishing to be bound by any theory, it is believed that this may be attributed to several factors. The elimination of adhesives eliminates an additional layer of material. In particular, it eliminates a relatively stiff material (the adhesive layer). In addition, it is difficult to spot bond such materials with adhesives. Adhesives are typically applied in layers or lines. These are generally less flexible arrangements than a pattern of dots due to their tendency to unduly restrict portions of the bonded materials from sliding past or over one another.

The actual flexibility of the sanitary napkin will, however, depend on the particular bonding pattern used. For example, if a plurality of very small, closely-spaced dots are used, the flexibility may not be any better than in products having adhesively secured layers, because closely spaced bonded areas make the bonded areas cover the overall area similar to a layer of adhesive. The flexibility may, on the other hand, be enhanced if the bonding pattern is in the form of a continuous or intermittent line if the line is oriented to create an axis about which the sanitary napkin can be bent.

The topsheet 28 and acquisition layer 34 may also be secured at least partially by any other suitable attachment means or combinations of such other means and the above attachment means. The topsheet 28 and the acquisition layer 34 can be at least partially attached by any means known in the art, such as by adhesives. If adhesives are used, the adhesives can be applied in a uniform continuous layer, a patterned layer, or an array of separate lines, spirals, or spots of adhesive. The adhesive attachment preferably comprises an open pattern network of filaments of adhesive as is disclosed in U.S. Pat. No. 4,573,986 issued to Minetola, et al. on Mar. 4, 1986, or an open pattern network of filaments comprising several lines of adhesive filaments swirled into a spiral pattern as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978; and U.S. Pat. No. 4,842,666 issued to Werenicz on Jun. 27, 1989. Suitable adhesives are manufactured by the Findley Adhesives Incorporated of Elm Grove, Wisc. and marketed as H-1077 or H-1137.

In still other embodiments, the topsheet 28 and acquisition layer 34 may be at least partially attached by mechanical and thermo-mechanical entanglement. The fibers of the acquisition layer 34 may be entangled in any of the manners specified above in forming the fiber-entangled film topsheet.

C. The Absorbent Core

The absorbent core 32 is positioned between the topsheet 28 and the backsheet 30. The absorbent core 32 provides the means for absorbing menstrual fluid and other body exudates. The absorbent core 32 is generally compressible, conformable, and non-irritating to the user's skin.

The absorbent core 32 can comprise any material used in the art for such purpose. Examples include natural materials such as cotton, comminuted wood pulp which is generally referred to as airfelt, creped cellulose wadding, peat moss, cross-linked cellulose fibers, absorbent foams, absorbent sponges, synthetic staple fibers, polymeric fibers, hydrogel-forming polymer gelling agents, or any equivalent material or combinations of materials.

In the embodiment shown in FIGS. 1–3, the absorbent core 32 is a laminate comprised of a layer of superabsorbent polymer material, such as in the form of particles, disposed between two air-laid tissues, first and second tissue layers (or "upper" and "lower" tissue layers). The first and second tissue layers provide containment of the superabsorbent polymer material, improve lateral wicking of the absorbed exudates throughout the absorbent core 32 and provide a degree of absorbency. A suitable laminate is the superabsorbent laminate WATER-LOCK L-535 available from the Grain Processing Corporation of Muscatine, Iowa (WATER-LOCK registered TM by Grain Processing Corporation). Such superabsorbent laminates are disclosed in U.S. Pat. No. 4,467,012 issued to Pedersen et al. on Aug. 21, 1984, and U.S. Pat. No. 4,260,443 issued to Lindsay et al. on Apr. 7, 1981.

The polymeric gelling agent which is employed in the absorbent core 32 will generally comprise particles of a hydrogel-forming polymer material. The term "particles", as used herein, can refer to particles in any form, such as in the form of pellets, flakes, or fibers. The characteristics of the absorbent core 32 (including, but not limited to the preferred types of polymer materials used therein, and types of methods which can be used for preparing these polymer particles) are described in greater detail in U.S. Pat. No. 4,673,402 issued to Weisman, et al, U.S. Pat. No. 5,009,653 issued to Osborn and the patents incorporated by reference in that patent, the disclosures of which are all incorporated by reference herein.

In a preferred version of the above embodiment, the absorbent core 32 is a laminate as described above which is slitted or partially slitted for longitudinal extensibility as shown in FIG. 15 on the accompanying drawing figures. This slitted or partially slitted core is described in greater detail in the Capillary Channel Fiber patent applications.

In another preferred version of the above embodiments, the absorbent core 32 is comprised of meltblown fibers. Such an absorbent core may be separately useful in absorbent articles that are not constructed with fused layers. (This also applies to the other cores and components described herein.)

The meltblown fibers are preferably treated to render them hydrophilic. Any suitable process used for rendering fibers hydrophilic can be used for this purpose.

This type of absorbent core 32 may be used to provide the sanitary napkin 20 with a bi-modal pore size distribution between the acquisition layer 34 (or other overlying layer) and the absorbent core 32.

The term "bi-modal pore size distribution", as used herein, refers to a distribution of pore sizes such that the overall pore size distribution of the absorbent core 32 material does not include a significant number of pore sizes in the same range as the acquisition layer 34 (that is, there is substantially no overlap in pore sizes between the two components).

Figure 20:
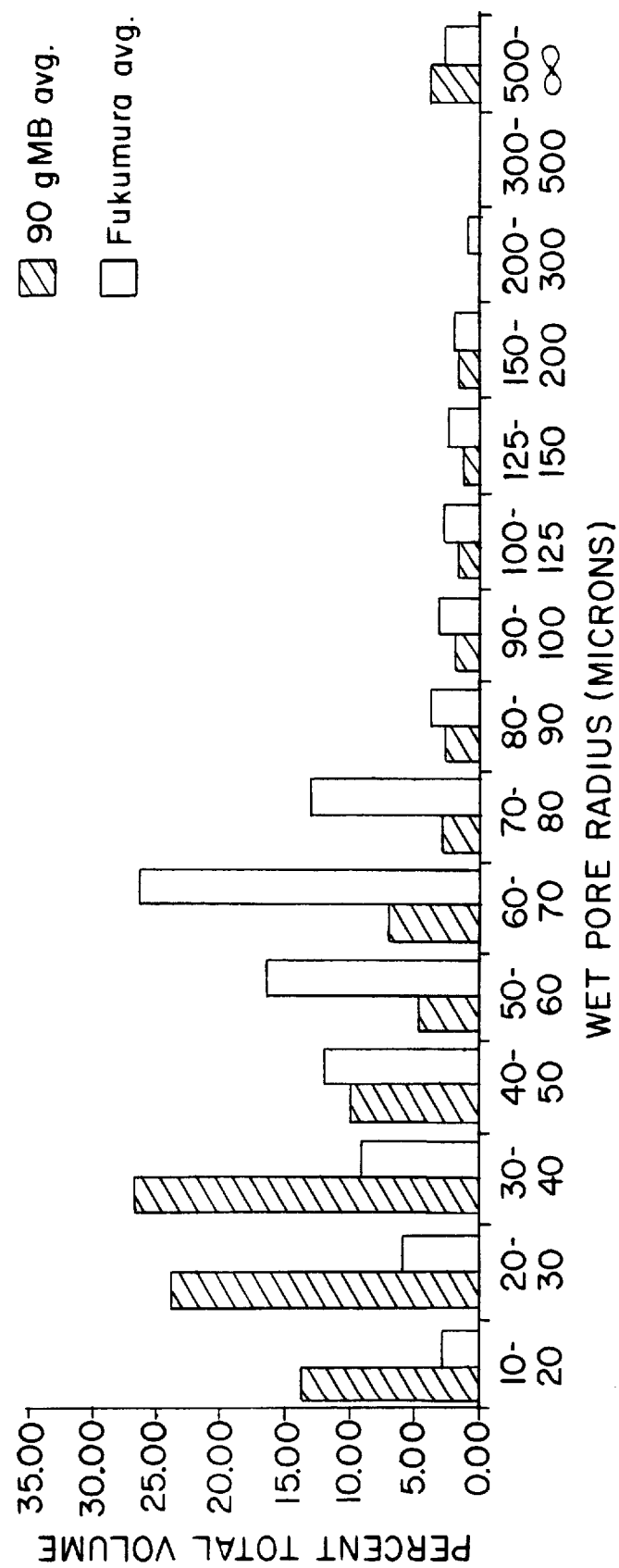
FIG. 20 is a graph which depicts a "bi-modal" pore size distribution.

FIG. 20 is a graph which shows an example of the pore size distribution of an acquisiton layer (the Fukamura material) and a meltblown absorbent core layer (designated "MB") FIG. 20 shows that the overall pore size of the absorbent core 32 should be less than the overall pore size distribution of the acquisition layer 34. The bi-modal distribution is particularly useful in establishing a capillary gradient between an upper layer or component and a lower or underlying layer or component.

The fibers used for the meltblown core can comprise any type of fibers that are suitable for use in meltblowing processes. Such fibers include, but are not limited to polyethylene fibers, polypropylene fibers, and nylon fibers. The fibers used in the meltblown core are preferably hydrophilic polyethylene fibers similar to those used in the fiber-entangled film shown in FIG. 7. Such fibers have a diameter ranging from about 1 to about 100 microns, preferably about 1 to about 20 microns. Such fibers are generally known as "micro denier" fibers since they have a denier per fiber of less than 1. Such fibers should have lengths of less than about 1.5 inches, preferably, such fibers have lengths of between about 0.01 inch and 1 inch.

The absorbent core 32 is preferably made from one or more webs of meltblown polyethylene fibers. Such a web or webs preferably have a basis weight of between about 60–180 grams/yd.$^2$ and an average wet pore radius size (which may be referred to as "average wet pore size radius", or for simplicity as "average wet pore size", or similar terms used herein) of between about 30–40 microns under no load, and an overall pore size distribution such that about 90% of the pores in the web have wet pore radii between about 10–80 microns under no load. The wet pore size radius is measured in accordance with the "Procedure for Liquid Extrusion Analysis" described injection 4 of this description.

Figure 21:
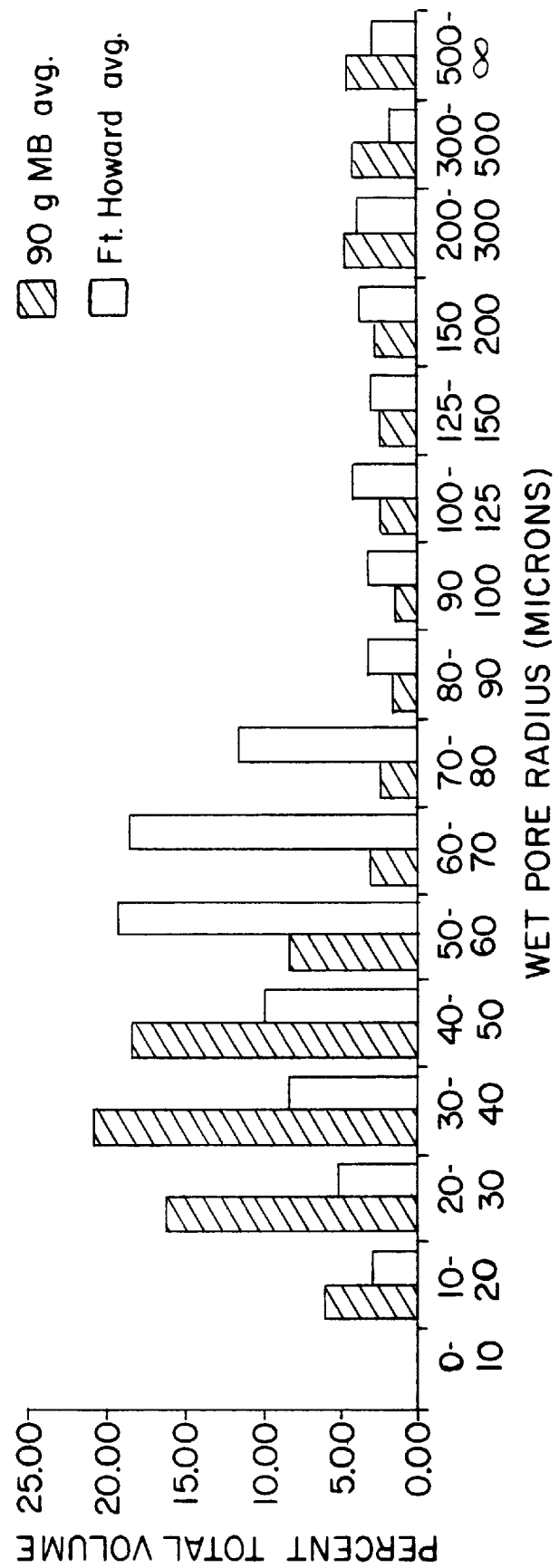
FIG. 21 is a schematic drawing that compares the small size pores present in the meltblown absorbent core materials described herein and the pore size of a conventional air laid tissue.
Figure 22:
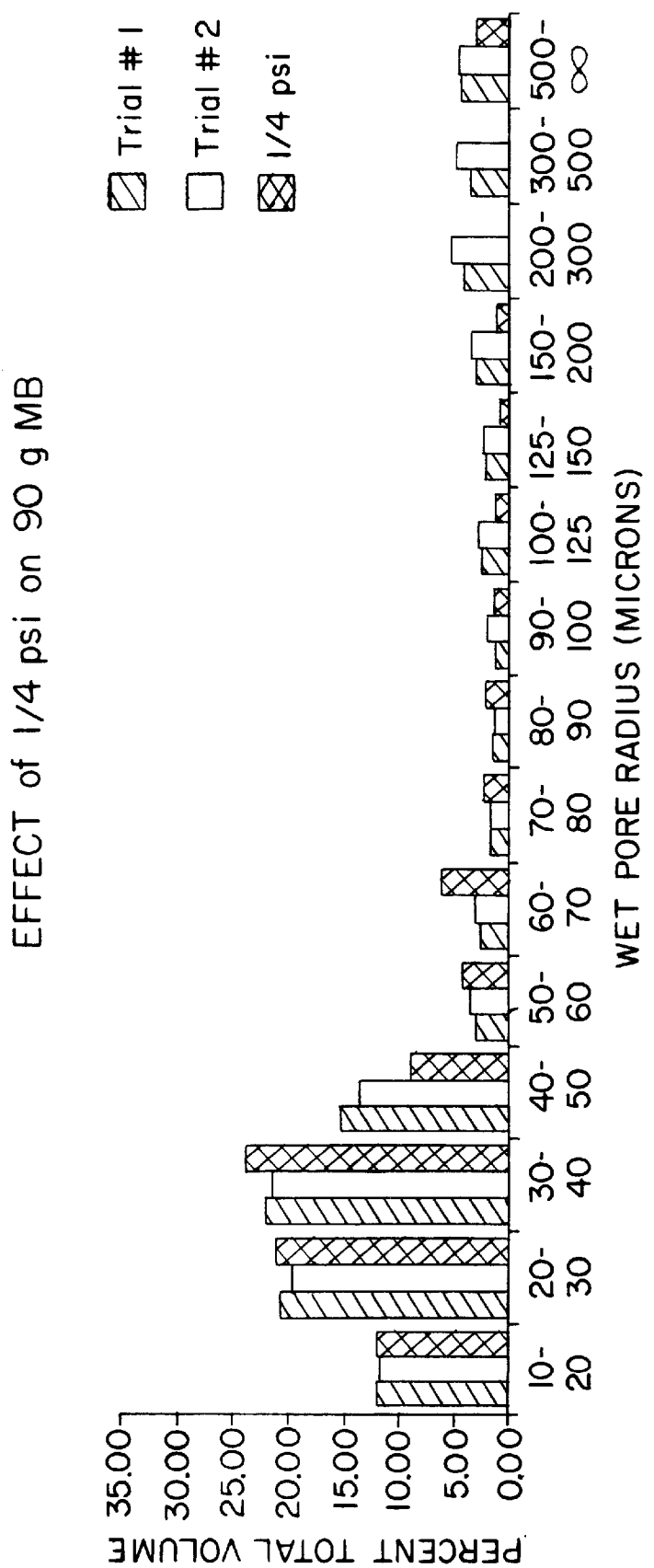
FIG. 22 is a graph which compares the wet pore radii size of a meltblown core under no load to that of the same core material under a load of 0.25 psi.

The meltblown construction provides the absorbent core 32 with smaller sized pores than are present in some of the tissue webs previously used in absorbent cores. These smaller pore sizes are compared to those of conventional air laid tissue core material (a Ft. Howard tissue) in FIG. 21. The meltblown fibers also make the absorbent core 32 resilient. In particular, the meltblown web is sufficiently resilient that the pores defined by the meltblown fibers tend to maintain their size when wetted and when they are placed under pressure. FIG. 22 is a graph that compares the pore size of a meltblown core material under no load (trials #1 and 2) to the same meltblown core material under a ¼ psi. (18 grams/cm$^2$) load.

The pores of the meltblown core are believed to retain at least about 90% of their pore size when under a load of ¼ psi (18 grams/cm$^2$). The smaller sized pores, combined with the tendency to retain the pore size under load provides the sanitary napkin 20 with a sustained capillary gradient from the topsheet 28 toward the absorbent core 32 and a sustained capillary distribution network within the absorbent core.

The sustained capillary distribution network within the meltblown absorbent core 32 referred to above can be summarized as follows. Typically, prior cellulosic absorbent cores had relatively small size pores. However, when liquids were deposited on such cores, the wetted cellulosic material would collapse. This would reduce the pore size of the wetted cellulosic material. The surrounding dry cellulosic material, however, retained its pore size. This caused the problem that the wetted cellulosic material would be surrounded by dry cellulosic material having larger sized pores. This destroyed the capillary distribution network within the cellulosic core to such an extent that it became difficult for liquids to be transported from their point of entry into the core to other portions of the absorbent core.

The meltblown cores of the present invention are believed to reduce or eliminate this effect. The meltblown cores are believed to provide a sustained liquid distribution network when wetted and when under pressure. This allows liquids to be transported to other parts of the absorbent core, and to make use of other parts of the core. This in effect, increases the effective storage capacity of the absorbent core when compared to absorbent cores comprised solely of cellulosic fibers.

Such behavior is especially apparent in the meltblown absorbent cores described herein. This is due to the improved resiliency and small capillary size of the meltblown core structure. The meltblown absorbent core structures described herein differ from absorbent cores made from other types of resilient materials. Other absorbent cores made of resilient materials were generally made from relatively large, strong resilient fibers. These fibers, while useful to create a resilient structure, created large pores in the structure. This had a negative impact on the capillary network of the absorbent core.

The meltblown absorbent cores 32 described herein can be in a non-limiting number of different arrangements.

In one embodiment, the absorbent core 32 can comprise a single layer or web having the basis weight specified above. The single layer can have superabsorbent material particles dispersed therein, e.g., in the form of a homogeneous blend, etc.

In another embodiment, the absorbent core 32 can comprise a laminate of superabsorbent material in the form of particles, fibers, or the like, between two meltblown fiber webs. As in the case of the tissue/superabsorbent material laminate, the meltblown material may be in the form of two separate webs, or it may comprise a single web of meltblown material C-folded or e-folded around the superabsorbent material. The core 32, in such an embodiment, is constructed similarly to the tissue and superabsorbent material laminate described above, only with the meltblown web or webs replacing the tissue webs.

In another embodiment, the absorbent core 32 can comprise a single layer or web having the overall basis weight specified above. In this embodiment, however, the web is provided with two or more regions having differing pore sizes. This embodiment can be made during the process of depositing the meltblown fibers to form the web. For example, a meltblowing process such as that shown in FIG. 18 could be used.

FIG. 18 shows that the fibers are deposited from a die 102 onto a surface. The die 102 is located a specific distance from the surface. The closer the die 102 is to the surface, the more densely the fibers will be deposited (under a given rate of airflow of fibers). The process used to make the embodiment described herein would typically use two or more dies located along the surface. These dies are located different distances from the surface. The meltblowing process will produce a single web with more dense areas (smaller pores) where the dies were located close to the surface, and less dense areas (larger pores) where the dies were farther away from the surface.

Figure 23:
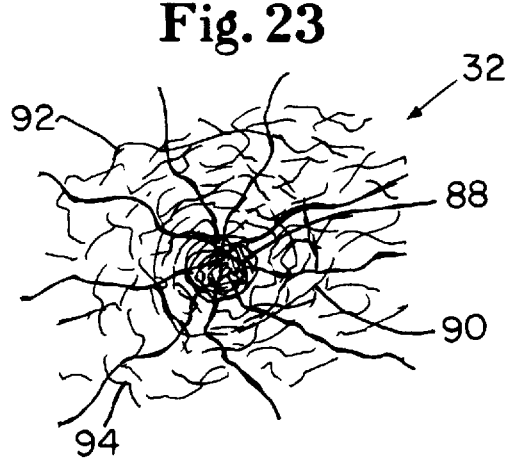
FIG. 23 is an enlarged schematic view of a portion of an absorbent core that is comprised of fiber flocked superabsorbent material particles encapsulated within meltblown webs.

In another embodiment, shown in FIG. 23, the absorbent core 32 can comprise superabsorbent material particles 88 having fibers 90 flocked thereon such as is described in U.S. Pat. No. 5,002,814 issued to Knack, et al. on Mar. 26, 1991. The use of such a material in the absorbent core 32 allows the inclusion of staple fibers such as polypropylene, polyethylene, PET, rayon, and cellulose fibers in the core with the superabsorbent material particles. Such fiber flocked superabsorbent material particles are preferably contained within a meltblown fiber matrix, such as between two layers of meltblown fibers 92 and 94.

The meltblown fibers in the layers may be fused to the fibers flocked onto the superabsorbent material particles. Alternatively, or additionally, the meltblown fibers in the two layers may be interlocked with or bonded to each other, and the fiber flocked superabsorbent material particles in between.

FIG. 23 (while not necessarily drawn to scale) shows that such an embodiment may be used to provide relatively large pores around the particles of superabsorbent material particles. These large pores provide space for the superabsorbent material particles to swell when they absorb liquids. This is believed to reduce incidents of gel blocking in the small pores of the meltblown network. The fiber flocked superabsorbent material particles are also believed to retain the superabsorbent material particles in place better, particularly when surrounded by a meltblown matrix. This reduces the undesirable tendency for such particles to come into contact with the wearer's skin.

In a variation of the embodiment described above, the absorbent core 32 can comprise a two or more layer structure comprising a meltblown layer and a second layer with superabsorbent material particles (fiber flocked particles, or superabsorbent material particles without attached fibers) in between.

The second layer could be a tissue web or a carded or spunbonded nonwoven web. The advantage of such a structure is that the superabsorbent particles or fiber flocked particles can be used to secure the layers together. These layers can be secured together by treating one or both of the layers that will be disposed adjacent the superabsorbent material particles with some suitable solvent, and then securing the webs using the fiber flocked or non-fiber flocked superabsorbent material particles and a combination of heat and pressure to induce permanent bonding. In this process, the superabsorbent material particles serve as a primary or secondary binder to fasten the layers together.

Figure 24:
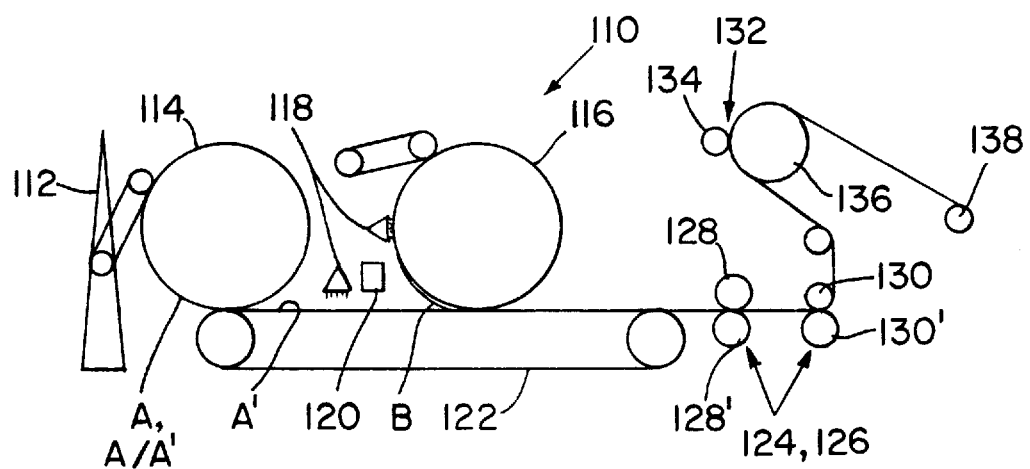
FIG. 24 is a schematic view of an apparatus and process for making a composite absorbent structure that uses superabsorbent material particles as a primary or secondary binder to attach two or more webs together.

FIG. 24 is a schematic diagram of an apparatus and process for making such a superabsorbent material laminate.

The preferred embodiment of the apparatus 110 comprises a first unwind stand 112, a first unwind roll 114 that feeds a web A into the process, a second unwind roll 116 that feeds a web B into the process, a pair of solvent applicators 118, a superabsorbent material particle applicator 120, a conveyor belt 122, two heat and pressure nips 124 and 126 formed between pairs of rollers 128 and 128' and 130 and 130', respectively, an embossing and drying nip 132 formed between two rollers 134 and 136, and an uptake roll 138.

Figure 25:
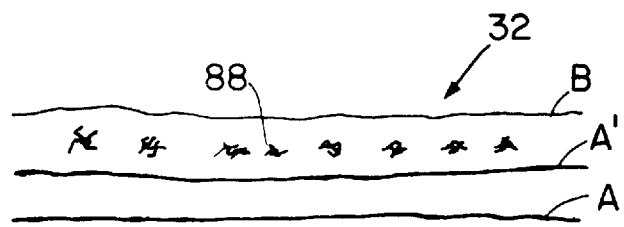
FIG. 25 is a schematic view of a preferred multilayer composite made with the process shown in FIG. 24.

In a preferred embodiment of this process, the solvent used is water. The first layer preferably comprises a dual layer composite designated A/A' in FIG. 24. Layer A comprises a web or layer of meltblown polyolefin fibers such as that described above. Layer A' is a layer that is used to tie to the superabsorbent material. Layer A' is positioned adjacent the superabsorbent material on the opposite side of the superabsorbent material from the second layer, B (FIG. 25). Preferably, layer A' comprises a layer of moisture absorbent fibers such as a web of nylon fibers known as Hydrofil available from Allied Signal, Inc., Hartford, Conn., or rayon fibers such as those available from Courtaulds Fibers, Ltd., West Midlands, England. The second layer, B, comprises an air laid or wet laid tissue layer.

The use of such an absorbent core 32 embodiment can further simplify the construction of the sanitary napkin. This embodiment eliminates the need for folding a tissue web into two layers to contain the superabsorbent material particles. It also eliminates the need for hot melt adhesives between these layers and may minimize any attendant stiffness caused by any other adhesives used therein. It can also simplify construction because the absorbent core material can be conveniently formed into a continuous web that can be separately fed into the process used during the construction of the sanitary napkin (that is, the core can be assembled off-line to simplify conversion into the final product).

In a further variation of such a product, layer B of the composite may serve as the topsheet or secondary topsheet (i.e., an acquisition layer) of the sanitary napkin. This will, in effect, provide a composite topsheet. This variation will further simplify the construction of the sanitary napkin 20, and will also allow the sanitary napkin to be made thinner, more flexible, and yet more resilient, for improved fit.

In any of the embodiments which use one or more webs of meltblown fibers, the web or webs could be provided with a feature that enhances the distribution of liquids. For instance, the web or webs of meltblown fibers could be embossed with a pattern of spaced apart lines that run in the longitudinal or machine direction to enhance the distribution of liquids in the longitudinal direction.

A meltblowing process can, in still another alternative embodiment, also be used for other purposes. For example, a meltblowing process can be used to seal the perimeter of an absorbent core, particularly one containing superabsorbent material particles. The perimeter can be sealed to prevent superabsorbent material particles from escaping from the core and coming in contact with the wearer's skin. Typically, in the past, this was done by wrapping the absorbent core in a tissue, or by folding the edges of the core, or by making the core from a folded laminate, and the like.

The meltblowing process, however, can be used to meltblow fibers onto those portions of the core that are disposed around the edges of the core. This will seal the edges. This alternative process can be carried out on cores made of a wide variety of materials, including cellulosic materials. It is not limited to cores made from meltblown fibers.

The meltblown absorbent core materials are particularly useful with the carded or spunbonded secondary topsheet materials described in Section 2B of this description.

The meltblown absorbent cores are particularly suitable for use with an acquisition layer 34 that comprises a hydrophilic spunbonded or carded polypropylene web having a basis weight of between about 16–32 grams/yd.$^2$ and an average wet pore size radius of between about 40–90 microns under no load and between about 20–80 microns under a ¼ psi. load, and an overall pore size distribution such that about 90% of the pores in the web have wet pore radii between about 20–125 microns under no load. Alternatively, the spunbonded or carded polypropylene web could comprise part of a composite topsheet material.

Figure 4:
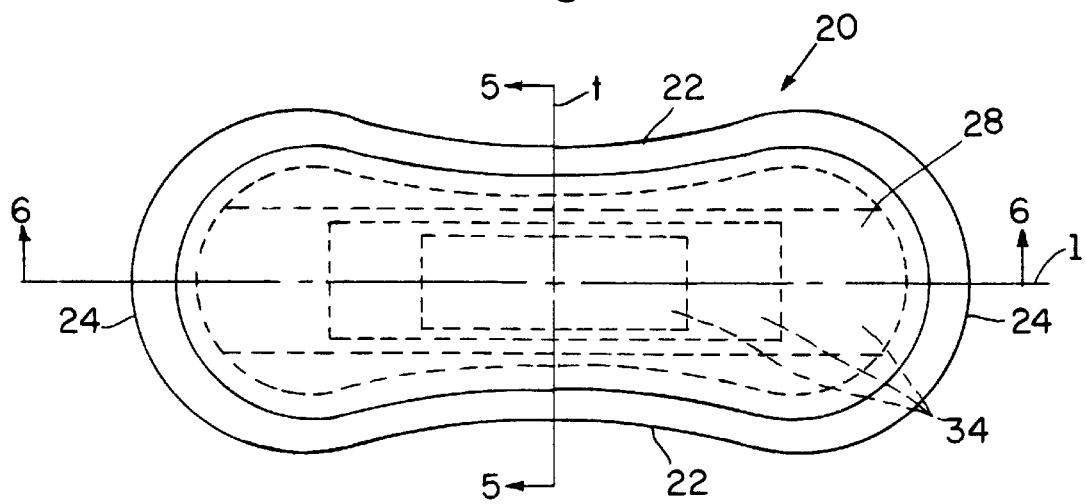
FIGS. 4–6 are top plan and simplified cross-sectional views along lines 5—5 and 6—6, respectively, of a thick sanitary napkin with a profiled shape.
Figure 5:
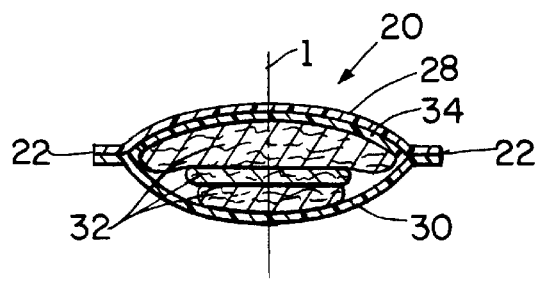
Figure 6:
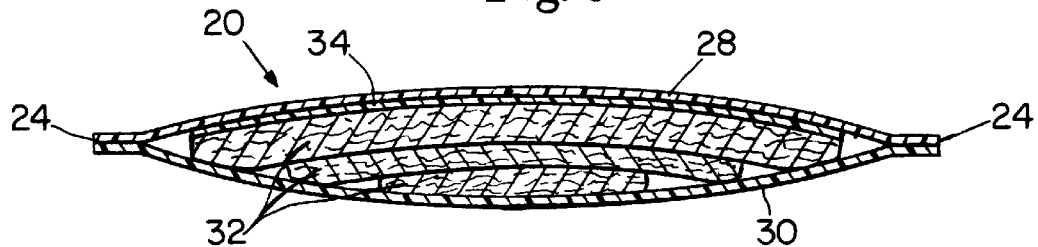

FIGS. 4–6 show one particularly preferred absorbent core 32 that will be referred to as a "blended" core. This particular core arrangement is shown in a relatively thick sanitary napkin 20. It can, however, also be formed into a thin web for use in thin products.

The blended absorbent core 32 comprises a batt of fibers, preferably in the form of a homogeneous blend of fibers. The blended core 32 is comprised of at least two groups (or types) of fibers. These include a first group (or type) of low denier, relatively short, hydrophilic fibers, and from about 5%, preferably at least about 10 or 20% to about 90% of higher denier, longer synthetic fibers that comprise a second group (or type) of fibers. The blend ratio of the two groups of fibers can be varied to produce the properties desired for different types of absorbent articles. (All percentages specified in this description are by weight unless stated otherwise.)

The first group of fibers can comprise natural fibers such as cotton, cellulose, or other natural fibers. The first group of fibers can alternatively or additionally comprise synthetic fibers, including but not limited to, rayon, chemical thermal mechanical pulp (or "CTMP" or TMP"), ground wood, or chemically modified fibers, such as cross-linked cellulose fibers. For one embodiment, the first group of fibers comprises comminuted wood pulp fibers known as airfelt. The fibers in the first group of fibers are either inherently hydrophilic, or they may be rendered hydrophilic by treating them in any of the manners described previously to render them hydrophilic.

Performance is improved by selecting a relatively stiff fiber which maintains a substantial portion of its compression resistance when wetted. (That is, the fibers should have a high compressive modulus.) Preferably, the fibers selected are both compression resistant and wet and dry resilient (i.e., they tend to both resist compression and to spring back when compressed). Cross-linked cellulose fibers are especially preferred for these criteria. (It is understood, however, that cross-linked cellulose fibers are sufficiently modified that they may no longer be considered as either cellulosic, or as natural fibers, per se.)

The second group of fibers should also be of high compressive modulus and should maintain a relatively high modulus when wetted. The second group of fibers should also preferably be wet and dry resilient. Suitable fibers include, but are not limited to synthetic fibers comprised of any of those materials specified above as being suitable for use as the fibers of the acquisition layer 34. (Fiber lengths, denier, etc. are, however, not necessarily the same. Some preferred fiber lengths, etc. are described below.)

The fibers in the second group of fibers are preferably longer than the fibers in the first group of fibers. Preferably, the fibers in the second group of fibers are greater than or equal to about ¼ inch (about 0.6 cm.) long, and are more preferably greater than or equal to about ½ inch (about 1.3 cm.) long. The denier of the fibers in the second group of fibers are preferably greater than the denier of the fibers in the first group of fibers. The fibers in the second group of fibers preferably have a denier per filament of between about 6 and about 40. More preferably, the denier is between about 15 and about 30, and most preferably between about 15 and about 25.

The fibers in the second group of fibers may be hydrophilic, hydrophobic, or partially hydrophilic and partially hydrophobic. The fibers in the second group of fibers preferably have at least some hydrophilic component (preferably a cellulosic component). The fibers in the second group of fibers can be provided with a hydrophilic component in a number of suitable ways. These include, but are not limited to coating or treating the fibers to render them, or at least their surfaces, hydrophilic.

One suitable type of synthetic fibers for use in the second group of fibers are crimped polyester fibers. Suitable synthetic fibers are available from Eastman Kodak Textile Fibers Division Kingsport, Tenn. as the KODEL 200 and 400 Series. One suitable type of synthetic fiber is the KODEL 410 fiber. A suitable polyester fiber is the KODEL 431 fiber. These KODEL fibers are preferably crimped at a crimping frequency of between about 5 and 7, preferably about 6, more preferably 6.3 crimps per linear inch (i.e., per 2.5 cm.). The fibers are preferably crimped at a crimping angle of between about 70° to about 91°, preferably about 88°. Crimping provides the fibers with improved resilience, among other desired properties. The fibers have a denier of 15 per filament and a length of about 0.5 inch (about 1.3 cm.). They may be coated with a hydrophilic or hydrophobic finish by any suitable method known in the art.

In an alternative embodiment, it is possible to replace the cellulose fibers in the first group of fibers with very short, low denier, synthetic fibers (with hydrophilic surfaces). The blended core 32 in this situation would consist of short, low denier, hydrophilic first group of synthetic fibers (such as polyester fibers with a CELWET finish) and long, high denier second group of synthetic fibers.

Such a blended core may also contain particles of hydrogel-forming polymer gelling agents to increase the absorptive capacity of the core.

In one preferred embodiment, the hydrogel-forming polymer gelling agents comprise "high-speed" absorbent gelling materials. The term "high-speed" absorbent gelling materials, as used herein, means those absorbent gelling materials that are capable of absorbing exudates at such a rate that they reach at least about 40%, preferably at least about 50%, and most preferably at least about 90% of their capacity in less than or equal to about 10 seconds. A suitable method for the percent rate of capacity is described in U.S. patent application Ser. Nos. 07/637,090 and 07/637,571 filed by Noel, et al. and Feist, et al. In alternative embodiments, it is also possible for the high-speed absorbent gelling materials to be mixed with other types (or ordinary speed) absorbent gelling materials.

Preferably, in the embodiment described immediately above, the high-speed absorbent gelling materials are in fibrous form. Such fibers (though not necessarily high-speed fibrous absorbent gelling materials) are discussed more fully in U.S. Pat. No. 4,855,179, issued Aug. 8, 1989, to Bourland, et al. The term "fibrous absorbent gelling materials", as used herein, is intended to include absorbent gelling materials in the form of fibers that are comprised entirely of absorbent gelling material and bi-component fibers that are comprised at least partially of other materials which have their surfaces coated with absorbent gelling materials. A suitable fibrous high speed absorbent gelling material is known as FIBERSORB SA7000 formerly manufactured by Arco Chemical Company of Newton Square, Pa.

The effective utilization of hydrogel-forming polymer gelling agents is believed to be improved in such a blended core. The use of higher concentrations of hydrogel-forming polymer gelling agents may also be possible.

The blended absorbent core 32 is preferably compressed to a density of at least about 1.5 g/cubic inch (about 0.09 g/cm$^3$). The blended core 32 may be compressed to densities at least as high as about 4.0 g/cubic inch (about 0.25 g/cm$^3$) to improve fluid wicking while still maintaining good softness and flexibility. (The density values specified above do not include the weight of any particles of absorbent gelling material.) Densification may be applied to the entire absorbent core 32 or only to selected portions. Patterned densification allows tailoring of the fluid handling properties to a specific need. For example, the density may be very low in the fluid target area to maximize fluid acquisition speed, and density may be very high near the core edges to maximize fluid wicking.

In one particularly preferred embodiment, the improved absorbent core 32 is an air-laid blend comprised of approximately 15% of 0.5 inch long, 15 denier per filament crimped polyester fibers and approximately 85% of cross-linked cellulose fibers compressed to a density of about 1 g/cubic inch (about 0.06 g/cm$^3$).

The blended absorbent core 32 can be used as the entire core or it can be used as one or more layers in a layered construction. The blended absorbent core 32 can be used with or without the acquisition layer 34.

FIGS. 4–6 show an example of a core 32 in which layers of core material are used to produce a "profiled" sanitary napkin 20. The profiled sanitary napkin 20 is thicker in the center of the sanitary napkin and tapers so it becomes thinner toward the edges 22 and 24. FIGS. 5 and 6 show that such a profiled sanitary napkin 20 can be made by stacking layers having relatively large length and width dimensions on top of those with smaller length and widths (or vice versa).

In a layered construction, one or more layers can consist of all cellulose or cellulose/hydrogel-forming polymer material blends. The layers could also have differing fiber and/or absorbent gelling material content. For example, a higher percentage of absorbent gelling material could be provided in the lower layers to provide additional liquid storage capacity.

The blended absorbent core 32 is believed to provide enhanced performance. The blended absorbent core is believed to provide improved fluid acquisition speed and absorptive capacity. These improvements are believed to result in reduced leakage. The absorbent core can also be made smaller and thinner to make the article more comfortable and discrete to wear. The strength of the core is also believed to be improved because of the synthetic fiber content. These improved characteristics are believed to be due to a number of factors.

Absorbent cores of the subject composition have a lower wet density than cores composed entirely of cellulose. The lower wet density results from the presence of the synthetic fibers. Water is not absorbed into the synthetic fibers, therefore, the modulus of the fibers does not change when wetted and they do not collapse. The lower wet density provides the blended absorbent core with improved fluid acquisition speed and higher absorptive capacity. The lower wet density allows any hydrogel-forming polymer materials included in the fiber matrix to absorb a higher quantity of liquids since there is more room for the polymer materials to swell.

The first group of fibers is believed to aid in reducing leakage. The blended core provides a quantity of small capillaries which a core comprised of 100% large synthetic fibers would not have. These smaller capillaries allow the core to pull liquids through the topsheet and away from the wearer's skin. This improves leakage performance due to a reduction in the volume of fluid which can exit the product by running along the skin surface.

The first group of fibers of the blended core also provides a wicking capability. This capability results from the small capillaries mentioned above. This capillarity can be enhanced by densification of the core. The cellulose allows the core to be maintained at a high density when dry that is generally not achievable with pure synthetics. The presence of the synthetic fibers allows the portions of the core that are wetted to expand and this reduces the density of these portions. The neighboring densified areas which are still dry have a high density and provide small capillaries. The liquids will, as a result, tend to wick into these neighboring areas. This maintains absorptive capacity and acquisition speed.

The crimped synthetic fibers are believed to provide the core with improved compression resistance and resiliency. The resiliency maintains the void space in the core even after liquids are absorbed into the core and pressure is applied to the core. The void space provides additional storage space for absorbed liquids. It also provides additional space in which the absorbent gelling materials can swell after taking in liquids.

The characteristics of other types of absorbent cores are described in greater detail in the patents and documents incorporated by reference herein. Additional characteristics are described in the patents and other documents incorporated by reference in those documents. The disclosures of all of these references are incorporated herein. In addition, other suitable absorbent core arrangements are described in U.S. Pat. Nos. 4,988,344 and 4,988,345, and European Patent Application Publication No. 0 198 683, published Oct. 22, 1986 in the name of Duenk, et al. Other possible core 32 materials are described in U.S. Pat. No. 4,475,911 issued to Gellert on Oct. 9, 1984.

The sanitary napkin (or other absorbent article) 20 could also include any additional layers or other components such as are described in the patents incorporated by reference. For example, the absorbent article may comprise an acquisition layer or patch of cross-linked cellulose fibers positioned between the topsheet 28 and the absorbent core 32.

D. The Backsheet

The backsheet 30 is impervious to liquids. The backsheet 30 serves to prevent menstrual fluid and other body exudates from soiling the clothing of the user. Any material used in the art for such purpose can be utilized herein. Suitable materials include embossed or nonembossed polyethylene films and laminated tissue. A suitable polyethylene film is manufactured by Monsanto Chemical Corporation and marketed in the trade as Film No. 8020.

In one alternative embodiment of the sanitary napkin 20 (typically in which the topsheet 28 overlays only the main body portion 21 and does not extend out to form the top surface of the flaps 36), the backsheet 30 may be comprised of two layers. In such a case, the backsheet 30 may comprise a first layer of lofted material disposed on the core-facing side 30a of the backsheet. The purpose of the first layer is to provide a comfortable, non-irritating surface against the body of the wearer. The lofted layer may be comprised of any suitable material, such as a nonwoven material. Preferably, the lofted layer comprises a hydrophobic nonwoven material. The second layer may be disposed on the garment side 30b of the backsheet 30, and may comprise a fluid impervious film. A low density polyethylene material about 0.01 to about 0.05 millimeters in thickness, preferably about 0.02 millimeters in thickness, has been found to work well as this second layer. A polyethylene film, such as is sold by the Ethyl Corporation, Visqueen Division, under model XP-39385 has been found particularly well suited for this second layer. The backsheet 30 may also be made of a soft, cloth-like material which is hydrophobic relative to the topsheet 28. A polyester or polyolefinic fiber backsheet 30 has been found to work well. A particularly preferred soft, clothlike backsheet 30 material is a laminate of a polyester nonwoven material and a film such as described in U.S. Pat. No. 4,476,180 issued to Wnuk on Oct. 9, 1984.

In other embodiments, the backsheet 30 is extensible. A particularly preferred extensible backsheet 30 is an extended adhesive film Formula #198-338 manufactured by the Findley Adhesives Company of Wauwatosa, Wisc. which is described in greater detail in the Capillary Channel Fiber patent applications.

As shown in FIGS. 1 and 2, the topsheet 28 is preferably secured to the backsheet 30 along a seam 64 around the periphery 26 of the sanitary napkin 20. The seam 64 can be formed by any means commonly used in the art for this purpose such as by gluing, crimping, or fusing. This is a preferred embodiment for ease of construction. (Other means of uniting the various elements can be used.) For instance, other possible embodiments include one in which the absorbent core 32 is essentially completely wrapped with topsheet 28 before it is placed on the backsheet 30. The sanitary napkin 20 can also comprise an absorbent core which possesses sufficient integrity to stand alone and is liquid pervious on one surface while the other surface has been treated to render it liquid impervious.

FIGS. 1 and 2 also show the fasteners, such as adhesive fastening means 38, which are adapted to secure the sanitary napkin 20 to the crotch region of an undergarment. Suitable adhesive fasteners are described in greater detail in U.S. Pat. No. 4,917,697. The fasteners used with the present invention are not limited to adhesive attachment means. Any type of fastener used in the art can be used for such purpose. For example, the sanitary napkin 20 could be secured to the wearer's undergarment by the fastener described in U.S. Pat. No. 4,946,527 entitled "Pressure-Sensitive Adhesive Fastener and Method of Making the Same" issued to Battrell on Aug. 7, 1990.

The adhesive fastening means 38 are covered by removable release liners, designated 40. The pressure-sensitive adhesives should be covered with release liners 40 to keep the adhesives from sticking to extraneous surfaces prior to use. Suitable release liners are described in U.S. Pat. No. 4,917,697. A suitable wrapper that both serves as a package for a sanitary napkin and as a cover for adhesives on the sanitary napkin is described in U.S. Pat. No. 4,556,146 issued to Swanson, et al. on Dec. 3, 1985.

3. Alternative Embodiments

There are also a number of possible alternative embodiments of the embodiments described above. A non-limiting number of these alternative embodiments are described below.

Figure 14:
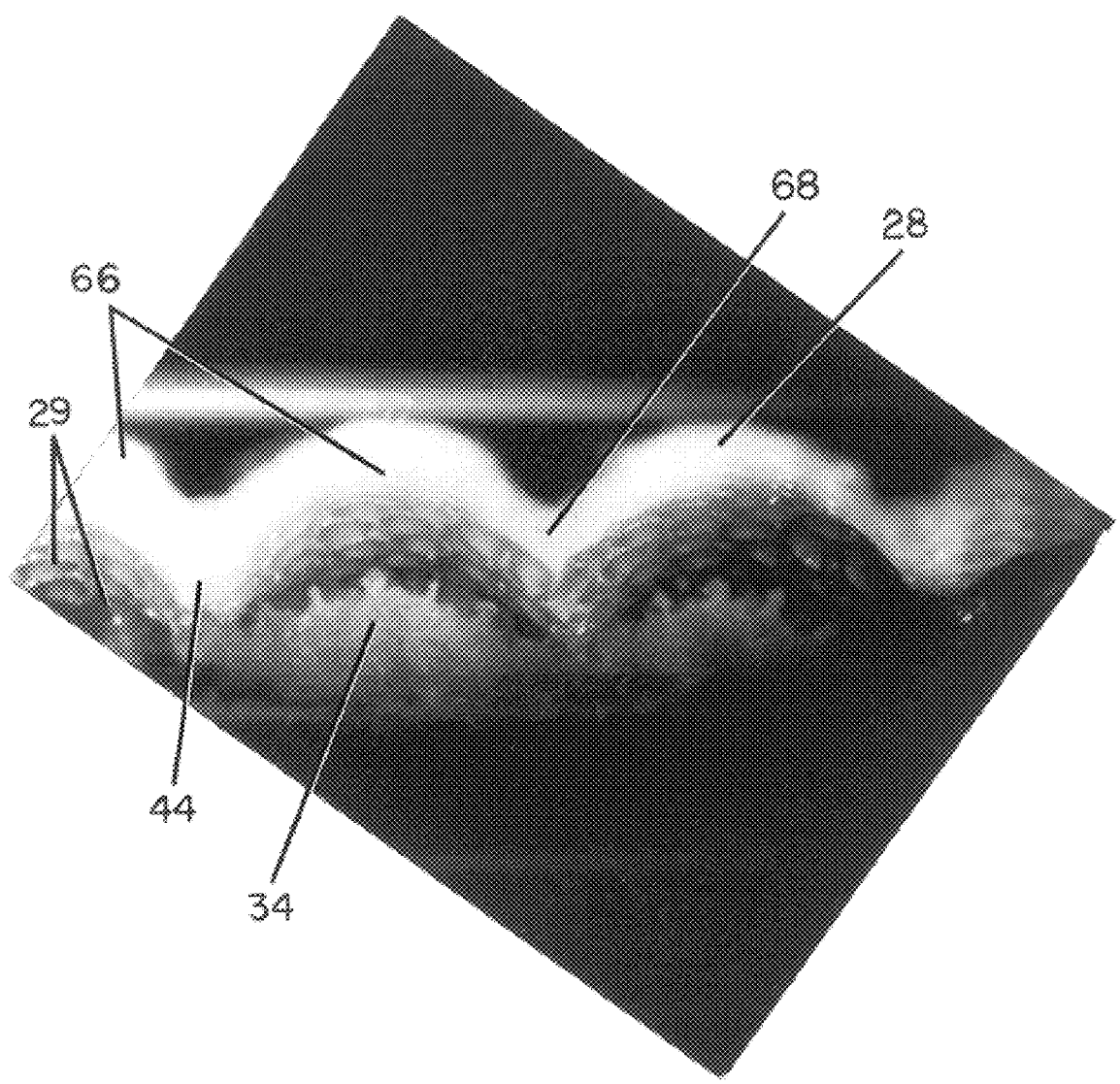
FIG. 14 is a photograph showing a cross-sectional view of an embodiment in which the underlying fibrous layer has been stretched prior to fusing it the apertured film.

FIG. 14 shows one alternative embodiment in which the acquisition layer 34 is stretched before it is fused to the topsheet 28. The topsheet 28 and acquisition layer 34 form a laminate. When the stretched laminate is relaxed, the laminate has tufted areas 66 formed therein between bonded areas 44 and valleys 68 at the bonds.

The embodiment shown in FIG. 14 provides a key advantage. It (and various alternative embodiments of that embodiment) allows a stretchable laminate to be formed from materials that are not ordinarily thought of as being stretchable. The apertured plastic film topsheet 28, for instance, is not normally thought of as being extensible. However, the topsheet 28 is provided with a degree of extensibility when it is secured to a layer such as the acquisition layer 34 after the acquisition layer 34 has been extended and bonded, and the two component materials are thereafter relaxed.

The tufted areas 66 in such a laminate can also provide certain benefits. The tufted areas 66 are typically soft. They will also place the absorptive fibers of the acquisition layer 34 closer to the wearer's body than the nontufted bonded areas. While not wishing to be bound by any particular theory, it is believed that this construction may enhance absorption (particularly at the tufted areas 66). The absorption of liquids in the z-direction (i.e., into the plane of the sanitary napkin 20) as well as the wicking of fluids in the x-y plane (in the plane of the sanitary napkin 20) may be enhanced. There may be several reasons for this.

The enhanced z-direction absorption is believed to result from the stretching of the acquisition layer 34. The stretching of an acquisition layer 34 made of meltblown or spunlaced fibers in the x-y plane causes the spaces between the fibers as measured in the x-y plane to increase in size. When the stretching forces are removed, the friction between the fibers makes it difficult for these types of fibers to return to their original position. The size of the spaces between the fibers are thus, permanently increased, making the acquisition layer 34 more permeable to liquids in the z-direction.

The wicking of liquids in the x-y plane is believed to be due to the provision of the valleys 68 formed between the tufted areas. In some embodiments, it may be desirable for the valleys 68 to run in the longitudinal direction so liquids will wick toward the ends of the sanitary napkin 20. In other embodiments, it may be desirable for the valleys 68 to run in the transverse direction so the laminate will be longitudinally extensible.

In other alternative embodiments, both the topsheet 28 and the acquisition layer 34 can be stretched prior to fusing the same together.

In another alternative embodiment, the fusion bonding may be used either as a primary means or a supplemental means of providing apertures 29 in the film topsheet 28. Prior to bonding, the topsheet 28 may be an unapertured film, or it may have less apertures than desired in the finished product. The apertures 29 could be formed by the device 74 shown in FIG. 8A. The fusion may, in the first case, form all of the desired apertures 29 in the topsheet 28. In the second case, the fusion may provide a number of apertures that supplements the number originally in the topsheet 28 to provide a total desired number of apertures.

Figure 17:
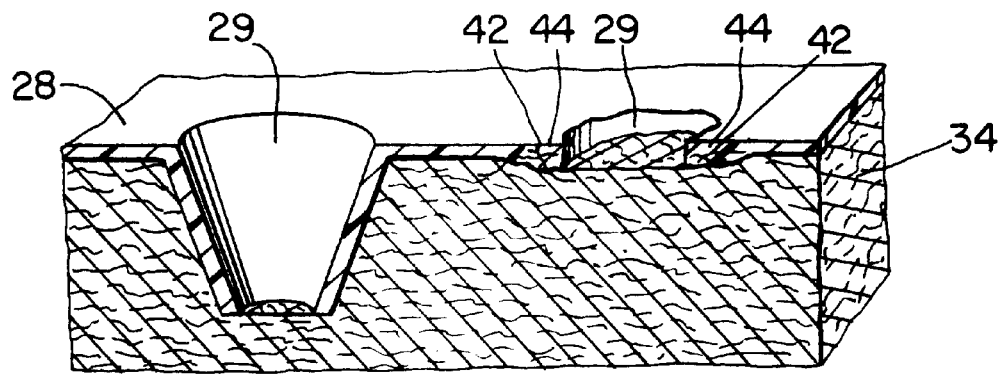
FIG. 17 is a perspective view of an alternative type bond structure.

In still another alternative embodiment shown in FIG. 17, the fusion could create a different type of bond structure.

FIG. 17 shows an embodiment in which a portion of the topsheet 28 is heated to cause it to become soft and pliant. The heated area of the topsheet 28 is subjected to a relatively high pressure to create bonded areas 44. The topsheet 28 is not heated enough that these bonded areas 44 are melted during the process. The topsheet 28 material, thus, does not flow together to completely close the apertures 29 in the bonded areas. Thus, the bonding forms bonded areas 44 in which the original apertures 29 provide the drainage passageways. The heating does, however, cause the three-dimensional film to collapse into a virtually two dimensional structure in the area of the bond 44. The heating may also cause the apertures 29 in the film 28 to assume irregular shapes.

The bonds 44 in FIG. 17 are formed when the pliant topsheet 28 material is forced into contact with the fibers 42 of the nonwoven. This causes the topsheet 28 material to become entangled around the fibers 42. As shown in FIG. 7, this may cause some fibers 42 to extend into apertures 29 or outward from an aperture 29.

A particularly preferred type of topsheet 28 material that can be used in the embodiment shown in FIG. 17 is a heat sealable film. Heat sealable films can be used to create such a bond 44 at lower temperatures and pressures. Heat sealable films are available with a layer or side that is heat sealable and another that is not. Such a film is usefull in that it could be placed with the heat sealable side adjacent the nonwoven layer and then bonded. Suitable heat sealable films are commercially available.

The embodiment shown in FIG. 17 is another example of a type of structure that will not interfere with the flow of liquids even though it may create a shallow bond having a fused area at the interface between the two bonded layers.

In another embodiment, the acquisition layer 34 can comprise a two layer composite structure. The two layer composite structure can comprise a structure that has a bi-modal pore size distribution within itself.

Such a structure could comprise a hydrophilic carded or spunbonded fabric polyester, polyethylene, polypropylene, or the like fabric that has meltblown fibers (such as those described above for use in the meltblown absorbent core) attached to its underside. Carded fabrics, as noted above, can be bonded in many different ways, such as thermally bonded, spunlaced, needlepunched, or powder bonded.

Alternatively, such a structure could comprise a meltblown web which is attached to the underside of the carded or spunbonded web by embossing or melt fusing.

Attaching hydrophilic micro denier fibers directly onto the underside of the carded or spunbonded fabric and the elimination of adhesives therebetween is also believed to improve the transportation of liquids into the absorbent core 32. This is primarily due to the strong capillary drive generated by the small pores of the meltblown fiber network that are made part of the acquisition layer.

Preferably, the meltblown fibers in such embodiments are deposited in a thin layer. The meltblown fibers are preferably deposited in a layer that does not exceed 30 grams/m$^2$. Preferably, the composite acquisition layer is also thin. Preferably, the basis weight of the composite does not exceed 50 grams/m$^2$. This will facilitate movement of liquids into the core, and will reduce the chance that they will tend to remain in this composite layer.

Meltblowing fibers directly onto the overlying carded or spunbonded fabric can also help during the fusion process. The presence of meltblown fibers, particularly if they have the same polymer chemistry as the topsheet, is very useful since these fibers are melt compatible with the topsheet. The outcome of such compatibility is higher bond strength between the topsheet and the acquisition layer.

Figure 26:
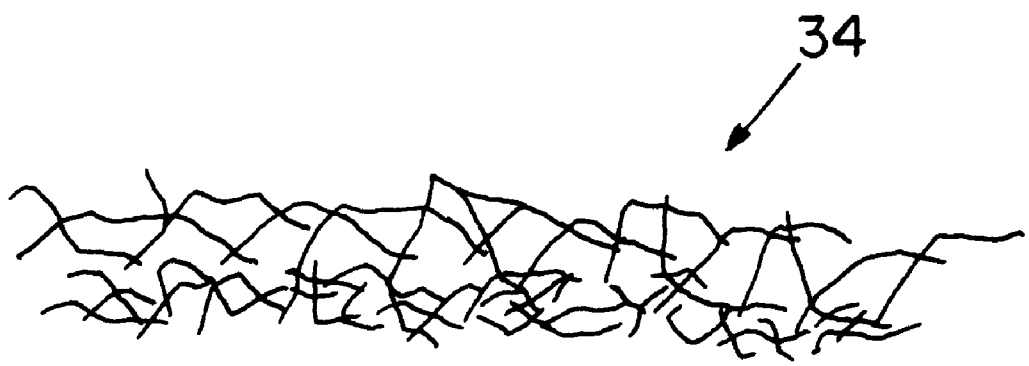
FIG. 26 is a meltblown acquisition layer having a bi-modal pore size distribution.

In a preferred alternative of the invention which is shown in FIG. 26, rather than comprising a two layer composite structure, the acquisition layer 34 could comprise a carded nonwoven web that is made from two or more groups of fibers having different deniers. For instance, the acquisition layer can be comprised of a first group of fibers that has a first relatively large denier (for example, a denier ranging from 2.2 to 6.0 denier per fiber) and a second group of fibers that have a second smaller denier (for example 0.1 to 2.2 dpf). This carded nonwoven could be constructed so that within the carded web, the first group of fibers lie above (nearest the topsheet) the second group of fibers. Such a construction has the advantage that a capillary gradient can be built into the acquisition layer 34 instead of having to secure two layers together to create a capillary gradient.

This variation preferably comprises a hydrophilic carded or spunbonded fabric that is preferably comprised of polyethylene, polyester, polypropylene, rayon, or acrylic acetate fibers. The carded or spunbonded fabric preferably has two different average wet pore size radii. The part of the structure containing the large denier fibers preferably has an average wet pore size of between about 50–140 microns under no load. The part of the structure containing the smaller denier fibers preferably has an average wet pore size of between about 7–50 microns under no load.

Any of these composite fabrics may, but need not be fusion bonded to the topsheet.

While several preferred sanitary napkin embodiments of the present invention have been described, numerous other types of sanitary napkins are available and are disclosed in the literature. These could be provided with the fused layers of the present invention. These sanitary napkins include those disclosed in U.S. Pat. No. 4,285,343, issued to McNair on Aug. 25, 1981; U.S. Pat. Nos. 4,589,876 and 4,687,478, issued to Van Tilburg on May 20, 1986 and Aug. 18, 1987 respectively; U.S. Pat. Nos. 4,917,697 and 5,007,906 issued to Osborn, et al. on Apr. 17, 1990 and Apr. 16, 1991, respectively; and U.S. Pat. Nos. 4,950,264 and 5,009,653 issued to Osborn on Aug. 21, 1990 and Apr. 23, 1991, respectively; and in U.S. patent application Ser. No. 07/605,583 filed Oct. 29, 1990 in the name of Visscher, et al.

The terms "pantiliner" or "panty liner" refer to absorbent articles that are less bulky than sanitary napkins which are generally worn by women between their menstrual periods. Suitable absorbent articles in the form of pantiliners that could be described with the used layers described herein are disclosed in U.S. Pat. No. 4,738,676 entitled "Pantiliner" issued to Osborn on Apr. 19, 1988.

The term "incontinent article" refers to pads, undergarments (pads held in place by a suspension system of same type, such as a belt, or the like), inserts for absorbent articles, capacity boosters for absorbent articles, briefs, bed pads, and the like, regardless of whether they are worn by adults or other incontinent persons. Suitable incontinent articles that can be provided with the fused layers described herein are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. patent application Ser. Nos. 07/637,090 and 07/637,571 filed respectively by Noel, et al. and Feist, et al. on Jan. 3, 1991.

The term "diaper" refers to a garment generally worn by infants and incontinent persons which is drawn up between the legs and fastened about the waist of the wearer. Suitable absorbent articles at least some of which are in the form of diapers which could be provided with fused layers are disclosed in U.S. Pat. Re. 26,152, issued to Duncan, et al. on Jan. 31, 1967; U.S. Pat. No. 3,860,003 issued to Buell on Jan. 14, 1975; U.S. Pat. No. 4,610,678 issued to Weisman, et al. on Sep. 9, 1986; U.S. Pat. No. 4,673,402 issued to Weisman, et al. on Jun. 16, 1987; U.S. Pat. No. 4,695,278 issued to Lawson on Sep. 22, 1987; U.S. Pat. No. 4,704,115 issued to Buell on Nov. 3, 1987; U.S. Pat. No. 4,834,735 issued to Alemany, et al. on May 30, 1989; U.S. Pat. No. 4,888,231 issued to Angstadt on Dec. 19, 1989; and U.S. Pat. No. 4,909,803 issued to Aziz, et al. on Mar. 20, 1990.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention. It is also expressly not admitted that any of the commercially available materials or products described herein teach or disclose the present invention.

The present invention, thus, provides absorbent articles having bonding between their layers, particularly their uppermost liquid pervious layers, that maintains sustained attachment even under prolonged use.

4. Test Methods

Bond Strength 180° Peel Test

The 180° Peel Test described below is used to ensure that the bonding between the fused layers is sufficiently strong so that the topsheet 28 will not separate from the underlying layer.

The 180° Peel Test essentially involves placing the fused layers in a tensile tester and applying forces to pull the layers apart. The test is referred to as a "180° peel" test because of the direction in which the peeling forces are applied. The sample is partially peeled and oriented so that the unpeeled portion of the sample and the layers to be peeled apart form a configuration that resembles two uppercase letter "L's" placed back to back. The peeling forces are then applied in opposite directions on the partially peeled components.

PRINCIPLE

The tensile tester is a device constructed in such a way that gradually increasing extension is smoothly applied to a defined sample, separating the layers, until one of the components of the sample fails (breaks) or the components separate.

SCOPE

This procedure is applicable to layered materials.

APPARATUS

Conditioned Room Controlled to 73 +/−2° F., 50 +/−2% relative humidity.

Oven Cole Parmer model N-05015-10. Cole-Parmer International, 7425 North Oak Park Avenue, Chicago, Ill. 60648 or equivalent.

Holding Stand An aluminum stand with 1 inch wide spring clamps.

J.D.C. Cutter Double edge cutter, 1 inch (25.4 mm) wide, equipped with safety shield. Thwing-Albert Instruments Co., 10960 Dulton Rd., Philadelphia, Pa., 19154, or equivalent.

Electronic Tensile Universal constant rate of elongation

Tester tensile testing machine with strip chart recorder, having a full range of 1000 grams, with other ranges available as necessary. Instron 1122 or 4201, Instron Engineering Corp., Canton Mass., or Thwing-Albert Intellect 500 or II, Thwing-Albert Instruments Co., 10960 Dulton Rd., Philadelphia, Pa., 19154 or equivalent.

Jaws Light duty, with line contact faces (barline). Obtain from appropriate instrument manufacturer as listed above.

SAMPLE PREPARATION

Sample according to the Sampling Instructions. Condition the samples in a conditioned room at 73+/−2° F., 50 +/−2% relative humidity for a minimum of 2 hours.

Label each sample in one corner for identification. Be sure not to label in such a way that the pen marks are in the area to be tested.

For samples to be tested in the Machine Direction (MD)

Using a J.D.C. cutter, cut four strips 1 inch (25.4 mm) in CD by approximately 6 inches (152.4 mm) in MD.

For samples to be tested in the Cross Machine Direction (CD)

Using a J.D.C. cutter, cut four strips 1 inch (25.4 mm) in MD by approximately 6 inches (152.4 mm) in CD.

INSTRUMENT PREPARATION

Calibrate and zero the tensile tester according to the manufacturer's instructions. Choose a load cell so that tensile results for the strip tested will be between 25% and 75% of the capacity of the load cell or load range used. This range is initially set to 500 grams full-scale.

Set the gauge length at 1 inch.

Set the instrument crosshead to operate at 22 inches per minute (+_2 inches per minute).

Set the chart speed at 5 inches per minute.

Set the tensile tester so that the crosshead travels for a distance of 10.4 inches. This will allow the tensile tester to monitor the forces generated while peeling the sample a total of 7.3 inches.

Zero the instrument so that the pen rests on the vertical zero line (distance axis) of the chart. Revolve the chart so that the pen also rests on one of the heavy horizontal lines (load axis) of the chart. Label the chart paper with the sample code, direction tested (MD or CD), date the test is being performed, full-scale load value, chart speed, crosshead speed, gauge length, and name of test (Bond Strength).

TEST PROCEDURE

By hand, separate approximately 1.5 inches of the sample on one end of the sample strip. Place approximately 0.5 inch of the one layer of the sample into the upper jaw of the tensile tester. Close the jaw. Place the remaining layer(s) into the lower jaw with enough tension to eliminate any slack, but not enough to move the pen off the zero mark. Close this jaw.

Start the tensile tester and recorder simultaneously as described by the manufacturer's instructions.

After the sample components separate (or one of the components fails (breaks), stop the chart and return the tensile tester to its initial starting position. Remove the sample from the jaws and position the chart for the next sample.

Repeat the procedure for each remaining sample strips.

CALCULATIONS/REPORTING

The most common points of interest in the analysis are the loads (grams force) at separation and at failure.

A. Bond Strength Force at Separation

For those instruments that are not able to capture and report the average forces of the sample separation, use a ruler as a straight edge and physically determine the average force of separation on the chart to the nearest gram. For those instruments that are capable of capturing and reporting forces, read the average force of separation from the digital display to the nearest gram.

B. Bond Strength Force at Failure

For those instruments that are not able to capture and report the peak force of the sample failure, physically determine the peak force of failure on the chart to the nearest gram. For those instruments that are capable of capturing and reporting forces, read the peak force of failure from the digital display to the nearest gram.

Average and report the four readings of average grams forces of the samples 1) separation and/or 2) peak force of the sample failure to the nearest gram. The bond strength force at separation is used to determine the average peel strength described above.

While particular embodiments of the present invention have been illustrated and described, it would be obvious to those skilled in the art that various other changes and modifications can be made without departing from the spirit and scope of the invention.

Procedure For Liquid Extrusion Analysis

Introduction

The Liquid Extrusion Analysis is useful for characterizing pore size distribution in absorbent structures.

The procedure for the Liquid Extrusion Analysis can be thought of as being analagous to the situation that occurs when a person wrings out a wet article of clothing to dry the same. Water is contained in the article of clothing in pores or pore-like structures of various sizes. To wring out the article, pressure must be applied to the article.

At the beginning of the wringing out process, a relatively large amount of water can be extracted from the article of clothing with relatively small amounts of pressure. As the process continues, however, greater and greater pressure is required to extract water from the article. At the same time, lesser and lesser amounts of water will be extracted. This reflects the fact that water was drained from the larger pores at the beginning of the wringing out process. At the end of the process, the water being removed from the article is coming from smaller pores, and is more difficult to remove.

Figure 27:
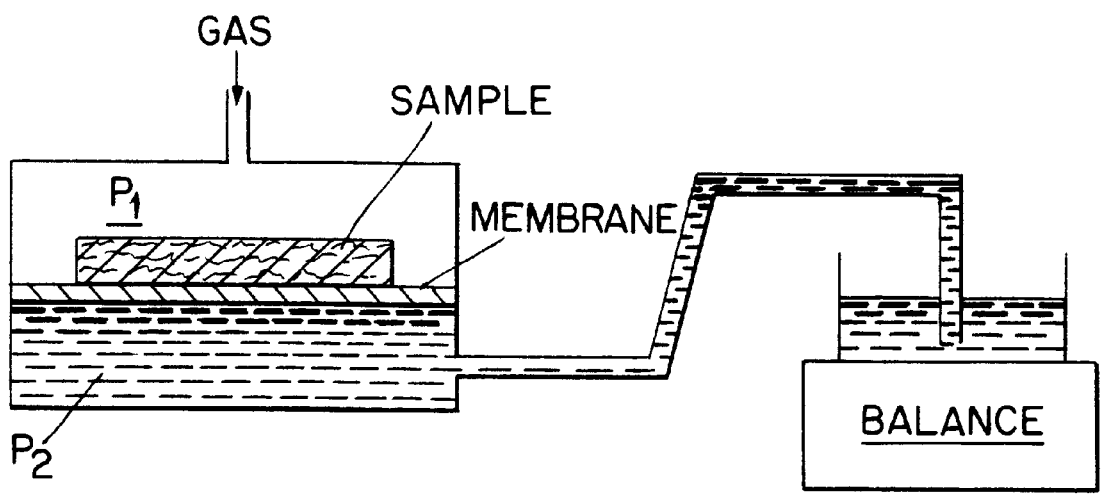
FIG. 27 is a schematic drawing of an apparatus for conducting the Procedure for Liquid Extrusion Analysis.

The Liquid Extrusion Analysis uses a pressure chamber to provide for controlled application of pressure on the article in issue (rather than a wringing out procedure). The liquid removed from the article (the sample) is extruded through a membrane, and weighed on a balance. The apparatus used in the Liquid Extrusion Analysis is shown schematically in FIG. 27.

The size of the radius of the pore drained at a given point in the conduct of the Liquid Extrusion Analysis is determined by employing the Laplace transform of the Washburn equation:

$$R = \frac{2 \text{ gamma } \cos(\text{theta})\text{adv(rec)}.}{DP}$$

where gamma is the surface tension of the fluid used; theta is the contact angle of the fluid and sample, either advancing or receding; R is the radius of the pore being drained; and delta P is the pressure change.

Briefly, the instrument consists of a pressure chamber in which the sample is placed, a hose or tubing connecting the vessel to a reservoir, the reservoir itself, and the balance on which it rests. The pressure chamber should be a Pore Volume Distribution Unit (or "PVD" unit or "liquid extrusion" unit) such as that manufactured by the TRI Company of Princeton, N.J., or equivalent. The pressure chamber has a series of grooves therein. The pressure chamber contains a set of membrane discs. The discs serve as the support and filtering media within the pressure vessel. A fluid runs through and in between both "halves" of the instrument.

Liquid extrusion analysis can be used to study pore volume distribution, hysteresis, swelling, compression, receding and advancing contact angles, surface pores, and multilayers.

The Initial Set Up

First, the pressure chamber must be thoroughly cleaned before exposing it to any test fluid. The hose should be set at a high enough level so the fluid will not flow out of the hose and into the reservoir during preparation. Fluid is initially placed in the reservoir as well as in the chamber, adding it slowly to avoid forming air bubbles.

Brand new discs should be cleaned in toluene for about two or three minutes to remove any residual oil present from its manufacture. A new steel disc should be sprayed with three coats of epoxy (paint). Discs previously coated with epoxy are sprayed only twice. Coats should be relatively light, spraying for approximately two seconds. The first one, or two in the case of a new disc, should dry for one half hour. The last coat applied before attaching the membrane should only dry for forty-five seconds.

If there is a reflective side to the membrane, that should be the side attached to the disc. If no reflective side can be discerned, either side may be used. After attachment, the disc and membrane are allowed to dry overnight on a soft surface, such as a paper towel, membrane face down, with a small (2–4 lb.) weight on top. The excess membrane hanging over the side of the disc is removed with a blunt blade, such as that of a screwdriver. Steel discs usually last for about twelve epoxy coatings. Membranes are usually changed because of age or punctures, the normal life of a membrane being two to three months if taken care of properly.

When changing membranes, the old membrane must first be scraped off the disc with a razor blade. Care must be taken that metal edges are not raised from the disc during the scraping motion. Acetone or methylene chloride is used to clean the residual paint from the disc.

Before being locked in the pressure chamber assembly, the disc and membrane must be soaked in test fluid. A soft foam is placed on pressure chamber before being primed with test fluid, adding fluid so the chamber holds a high level of fluid. The metal securing ring may need to be added to contain a level of fluid that is high enough to cover the disc. The disc is set on the foam, membrane side down, such that the disc is only half immersed in fluid.

After waiting for a few moments for the air to escape from the disc, the arrangement is then totally submerged by adding more test fluid. Again waiting a bit for air to escape, the disc is carefully taken out of the pressure chamber and quickly inverted, the whole motion lasting only a split second. The foam is then removed, and the disc is carefully placed right side up in the chamber. Air bubbles which congregate near or over the membrane and pressure chamber interface must be removed with an eyedropper.

A plastic shield should be fashioned to suspend over, but not touch, the membrane while fastening screws, etc. This will protect the membrane from damage while assembling the chamber. It is of paramount importance that the membrane must never, ever be touched. Touching the membrane will cause a micro-puncture in the membrane that will greatly affect test results. A camel's hair paint brush should be used to clean the membrane of any residual fibers from samples. Also, the paint brush can be used to remove the samples from the pressure chamber after a test has been run.

Priming the system, or gaining suction between the pressure chamber and reservoir, should be done carefully and without the help of any artificial pressures. The level of the glass tubing is simply lowered until the fluid starts to flow towards the opening where the tubing is attached to the reservoir over the balance. Right after fluid starts to emerge from the opening, the glass tubing is placed in the reservoir, below the surface of the fluid. It can then be securely clamped down. There should be no air caught between the opening of the tube and the reservoir. Any air bubbles floating in the reservoir must be removed by using an eyedropper. Any air bubbles caught in the tubing must also be removed by raising and lowering the tubing, forcing the air bubbles to the pressure chamber and out the leveling cylinder.

Next, the excess fluid remaining from soaking the disc should be removed from the pressure chamber. This is done by opening the valve that drains fluid from the most outboard groove of the pressure chamber. After the disc and membrane are in place with the level of fluid in the pressure chamber below that of the membrane, the o-ring and then the metal securing ring are carefully placed on top of the disc.

The top surface of the metal securing ring must be wiped clean of test fluid. Otherwise test fluid can enter the inside of the pressure chamber and affect test results. Fluid which enters the screw holes of the metal securing ring while soaking the disc must be removed with an eyedropper. Some residual test fluid in the groove around the pressure chamber is beneficial since it prevents condensation on the inside of the pressure chamber. Once all is set, the level of the pressure chamber is adjusted so that the level of the meniscus in the leveling cylinder is exactly even with its opening, and equilibrium is then awaited. When it is approximately reached, the screw can be put into the leveling cylinder.

A small plastic disc should be placed in between the reservoir and balance to prevent tilting and provide greater stability. The hose up to the balance should be allowed to follow a natural path, avoiding any curves or bends. The path should also be devoid of any major dips or crests; this alters the equilibrium of the flow. Once a path has been set for the tubing, it should be maintained constant as best it can. It should be free standing, so that any vibrations will not affect the measurement at the balance. The glass tubing which deposits the fluid in the reservoir should, however, be capable of being securely clamped down to prevent vibrations from traveling to the reservoir.

Use of the Liquid Extrusion Unit

Before any testing is done, a blank run should be made with the apparatus. This entails running a test with no sample at possible pressures at which one might want to measure. This blank run calibrates the apparatus to take into account the fluid which is unavoidably trapped in the chamber top, especially in the meniscus between the o-ring and the membrane.

Before running tests, this membrane o-ring interface should be very gently blotted with a paper towel to remove any large amounts of fluid. Blanks should typically be no larger than two or three tenths of a gram. Trapped air in between the membrane and the disc is a source of error, causing variability in the blank. If, while making a blank run, the fluid mass on the balance seems to be endlessly increasing, never tapering off, there is hole in the membrane. In such a case, the membrane must be changed.

When running samples that hold more than a couple of grams of fluid, one may want to presaturate the sample and then place it in the pressure chamber. For this purpose, it is useful to have a plastic holder on which to place the sample while soaking it. Also, it is a good idea to slide the sample off the holder with the brush, as this allows one not to touch the membrane. Any excess fluid should then be gently blotted away with a paper towel. An attempt to remove every last bit of fluid should not be made; the small excess which can not be removed with a paper towel will soak down into the disc.

Whether the sample is presaturated or allowed to wick fluid back from the reservoir, the apparatus must reach a certain level of equilibrium, i.e., a steady state, before starting the test. This means that the mass on the balance is only changing by a definite amount, as discussed below. After this, a test can be started.

The PVD is an equilibrium instrument. All tests must be started and executed at a predetermined level of equilibrium. An "equilibrium constant" must be chosen for this particular level of equilibrium. This number refers to the maximum rate at which fluid extrusion is considered trivial. This number is dependent on the degree of accuracy required. It is more of a rule of thumb than it is a constant. The supplier of the PVD unit suggests a rate of 2 mg/min for every 1000 mm$^3$ of fluid extruded from the sample. For example, the equilibrium rate for a sample which holds one gram of fluid would be $$\frac{1 \text{ g } (1 \text{ cm}^3) (10^3 \text{ mm}^3) (2 \text{ mg/min}) (1 \text{ min})}{(1 \text{ g}) (1 \text{ cm}^3) (1000 \text{ mm}^3) (60 \text{ sec})}$$

since 1 g is the amount extruded, 1 cm$^3$/g is the density of the fluid, there are 10$^3$ mm$^3$ in 1 cm$^3$, the suggested rate is 2 mg/min per 1000 mm$^3$, and there are 60 sec in one min. The above example works out to a rate 0.033 mg/s. Since the balance only reads to the nearest 0.1 mg, an equilibrium rate of 0.1 mg/s would probably be sufficient. For a typical thick absorbent core that holds ten to fifteen grams of fluid, this works out to be about 0.4 mg/s. Also, it has been suggested that this equilibrium rate be maintained for at least thirty seconds.

Practically, what this means is that one simply sets the desired pressure, waits for the balance to slow down to the determined equilibrium rate, waits for thirty seconds, and finally records the mass on the balance.

The pressure should be adjusted gradually and carefully. Target pressures should always be approached from the same direction; if the pressure is being increased, it should always be approached from a lower pressure, and vice versa. This restriction is because advancing and receding contact angles are different, and the same contact angle should be involved at each step of the test.

Analysis of Data

There are two major ways of displaying data in graph form. The first, the volume distribution vs. radius, gives a quick break down of the pore volume distribution of a material. The second, the cumulative plot of total volume vs. radius conveys more information but less quickly.

Plotting percent volume extruded vs. radius yields the volume distribution graph. Typically, bar graphs are used with the percent volume on the y axis and the radius ranges on the x axis. This is the first derivative of the cumulative plot. See FIGS. 20 and 21.

Composing the cumulative plot involves representing the total volume extruded per gram sample on the y axis and the radius range on the x axis. This graph indicates the total volume or capacity per mass of the sample, while the volume distribution graph does not.

What is claimed is:

1. An absorbent article having a longitudinal centerline, said absorbent article comprising:

a liquid pervious apertured thermoplastic film topsheet, said topsheet having a core-facing face;

a liquid impervious backsheet joined to said topsheet;

an absorbent core positioned between said topsheet and said backsheet; and a fibrous acquisition layer comprised of at least some synthetic fibers, said acquisition layer being positioned between said topsheet and said absorbent core, said acquisition layer having a body-facing face and comprising a folded sheet which has been folded so that a double z-fold structure is formed, wherein when said double z-fold structure is viewed in cross-section taken along a transverse line it is divided into a left half and a right half by the longitudinal centerline, and the left half of the folded sheet appears as a reverse letter "z", and the right half appears as a letter z;

wherein the core-facing face of said topsheet is adjacent the body-facing face of said acquisition layer and said topsheet is fused to said acquisition layer at discrete bonded areas, at least some of said bonded areas providing structures with drainage passageways for liquids to pass through to said absorbent core.

2. The absorbent article of claim 1 wherein said absorbent article comprises a longitudinal central region located along said longitudinal centerline and being centered about said longitudinal centerline, and longitudinal side regions laterally outboard of said longitudinal central region, wherein said bonded areas are located in both said longitudinal central region and said longitudinal side regions, said bonded areas having a circular plan view shape, and said bonds located in said longitudinal central region are larger than said bonds located in said longitudinal side regions.

* * * * *